(12) United States Patent
Boschetti et al.

(10) Patent No.: US 7,754,861 B2
(45) Date of Patent: Jul. 13, 2010

(54) METHOD FOR PURIFYING PROTEINS

(75) Inventors: Egisto Boschetti, Croissy sur Seine (FR); Lee O. Lomas, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 24 days.

(21) Appl. No.: 11/388,181

(22) Filed: Mar. 22, 2006

(65) Prior Publication Data

US 2006/0216751 A1 Sep. 28, 2006

Related U.S. Application Data

(60) Provisional application No. 60/664,794, filed on Mar. 23, 2005.

(51) Int. Cl.
*A23J 1/00* (2006.01)
*C07K 14/00* (2006.01)
*C07K 17/00* (2006.01)
*C40B 40/10* (2006.01)

(52) U.S. Cl. .......................... 530/412; 530/350; 506/18

(58) Field of Classification Search ................ 530/412, 530/350; 506/18
See application file for complete search history.

(56) References Cited

U.S. PATENT DOCUMENTS

| | | | |
|---|---|---|---|
| 5,010,175 A | | 4/1991 | Rutter et al. |
| 5,013,669 A | | 5/1991 | Peters, Jr. et al. |
| 5,075,423 A | * | 12/1991 | Balint, Jr. .................... 530/350 |
| 5,491,084 A | * | 2/1996 | Chalfie et al. .................. 506/10 |
| 5,719,060 A | | 2/1998 | Hutchens et al. |
| 5,849,535 A | * | 12/1998 | Cunningham et al. ...... 435/69.4 |
| 6,139,746 A | | 10/2000 | Kopf |
| 6,225,047 B1 | | 5/2001 | Hutchens et al. |
| 6,348,318 B1 | | 2/2002 | Valkirs |
| 6,670,142 B2 | | 12/2003 | Lau et al. |
| 6,844,426 B2 | | 1/2005 | Nishiya et al. |
| 2001/0034053 A1 | | 10/2001 | Winge |
| 2002/0127739 A1 | | 9/2002 | Pieper |
| 2003/0036095 A1 | | 2/2003 | Tchaga |
| 2003/0211471 A1 | | 11/2003 | Hammond et al. |
| 2003/0212253 A1 | | 11/2003 | Hammond et al. |
| 2004/0082047 A1 | | 4/2004 | Emery et al. |
| 2004/0101830 A1 | | 5/2004 | Hammond et al. |
| 2004/0106180 A1 | | 6/2004 | Blank |
| 2004/0115169 A1 | | 6/2004 | Wolfe et al. |
| 2004/0115785 A1 | | 6/2004 | Fong et al. |
| 2004/0180415 A1 | | 9/2004 | Tchaga et al. |

FOREIGN PATENT DOCUMENTS

| | | |
|---|---|---|
| EP | 1006362 A1 | 7/2000 |
| WO | WO 99/06833 A1 | 2/1999 |
| WO | WO 2004/031730 A2 | 4/2004 |

OTHER PUBLICATIONS

Cunningham et al., Experimental Cell Research, vol. 259: 239-246; Apr. 10, 2000.*
Definition for "different" from American Heritage Dictionary of the English Language; downloaded from www.bartleby.com on Aug. 1, 2008.*
Freije Jr., et al., "Activity-based enrichment of matrix metalloproteinases using reversible inhibitors as affinity ligands"; Journal of Chromatography A, Elsevier Science, NL; vol. 1009, No. 1-2; pp. 155-169; XP004447858; ISSN: 0021-9673 (Aug. 2003).
Ferrer I., et al.; "Validation of new solid-phase extraction materials for the selective enrichment of organic contaminants from environmental samples"; TRAC, Trends in Analytical Chemistry, Analytical Chemistry; Cambridge, GB; vol. 18, No. 3, pp. 180-192; XP004161232: ISSN: 0165-9936 (Mar. 1999).

* cited by examiner

*Primary Examiner*—Sue Liu
(74) *Attorney, Agent, or Firm*—Townsend and Townsend and Crew LLP.; M. Henry Heines

(57) ABSTRACT

The present invention provides methods and kits for purifying a target protein group. The method comprises the steps of contacting a sample comprising at least 95% of the target protein group and at most 5% of contaminating proteins with a library of binding moieties having different binding moieties, binding the contaminating proteins and a minority of the target protein group to the library of binding moieties, separating the unbound target protein group from the proteins bound to the library of binding moieties and collecting the unbound target protein. The collected target protein is more pure than the target protein group in the sample.

30 Claims, 3 Drawing Sheets

A

B

METHOD FOR PURIFYING PROTEINS

CROSS-REFERENCE TO RELATED APPLICATIONS

This application claims benefit of provisional application Ser. No. 60/664,794, filed Mar. 23, 2005, the disclosure of which is incorporated in its entirety herein by reference.

FIELD OF THE INVENTION

The present invention relates to the fields of combinatorial chemistry, protein chemistry and biochemistry. Particularly, the present invention describes methods and kits for use in the field of protein purification.

BACKGROUND OF THE INVENTION

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, proteins and growth factors, usually supplied from preparations of animal serum. Concomitantly to the expression of the target protein many other proteins are also produced. Isolation of the desired protein from the mixture of compounds fed to the cells and from the by-products of the cells themselves to a level of purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire protein contents of the cell into the homogenate, increasing even further the difficulty to isolate the target protein. The same problem arises, although on a smaller scale, with directly released proteins due to the natural death of cells during the culture process.

Once a clarified solution containing the protein of interest has been obtained, its separation from the other proteins produced by the cell is usually attempted using a combination and sequential application of different chromatography techniques. These techniques separate complex mixtures of proteins on the basis of their charge, degree of hydrophobicity, size, or affinity. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through." However, often a purified protein solution containing a protein of interest still also contains a variety of contaminating proteins and other undesirable impurities—albeit at a lower amount than in the starting material for purification. Current attempts to overcome this problem typically involve a so-called polishing step. This step often involves gel filtration, for example, when the contaminating proteins have a molecular weight different from the target protein, immunoaffinity chromatography, or ion exchange chromatography.

Immunoaffinity chromatography is most useful when all contaminating proteins present in a sample are known and when antibodies against those contaminating proteins are available. Typically, antibodies are then immobilized to a solid support and used as immunosorbents. However, there are substantial drawbacks to this approach. Very often, the identity of the contaminating proteins is not known and thus, this antibody approach is not feasible. In addition, immunoaffinity columns are expensive and seldom totally specific for their target.

Anion exchange chromatography is a general approach and often used to remove endotoxins and foreign DNA, both relatively acidic molecules. This approach also binds other molecules that are acidic, such as certain proteins. However, this approach is ineffective for removal of contaminating proteins that have characteristics (e.g., same net charge) similar to a target protein of interest.

Thus, very often, contaminating proteins whose properties are not known are very difficult to remove. In the case of therapeutical protein solutions even trace amounts of contaminating proteins may have a disastrous effect on a patient to whom such therapeutical protein is administered. Such effects include severe allergic or immunological reactions. Often these effects are caused by contaminating proteins that are derived from eukaryotic or prokaryotic cells that are used to recombinantly express the therapeutical protein. These contaminating proteins are known as HCPs (Host Cell Proteins). HCPs, by definition, are very diverse and using methods of the prior art cannot be removed in a single process. Therefore their elimination is contingent upon a series of steps that also contribute to the reduction of the overall yield of the therapeutical protein of interest. Thus, methods whereby all contaminating proteins or impurities are at least partially, preferably completely, removed in a single purification step are preferred over the prior art methods.

BRIEF SUMMARY OF THE INVENTION

It is an object of this invention to remove as many impurities from an already highly purified sample as possible. Certain kinds of libraries of binding moieties are preferred for achieving this end. In particular, one can best achieve this end by using libraries of large numbers of different binding moieties that have not been pre-selected for their ability to bind particular analytes in a sample. Such libraries are referred to herein as "non-selective" libraries. (The fact that binding specificities of some binding moieties in such a library may be apparent after using the library does not render the same library "selective.") Using such libraries increases the likelihood of capturing species throughout the population without discrimination. Thus, for example, a library of antibodies in which each antibody is directed to a known binding partner will select only the species to which each antibody is directed; in contrast a germ line antibody library of the same size does not contain antibodies that bind to pre-selected analytes. Such a library is more likely to select species not known to exist in a sample. One can create non-selective libraries by employing combinatorial chemistry or by randomly assembling chemical moieties. Furthermore, by increasing the size of a library, whether selective or non-selective, one can increase the number of different analyte species in a sample captured and detected. Examples of non-selective libraries of binding moieties include germ line antibody libraries, phage display libraries of recombinant binding proteins, dye libraries, combinatorial libraries based on peptides, oligonucleotides, oligosaccharides, and non-combinatorial libraries in which the binding specificity of the members is not pre-selected, combinatorial libraries of various sorts and portions thereof. It should also be noted that the amount of purification depends upon the relative amounts of binding moieties and contaminants in the sample. The relative amount of binding moieties to contaminants should be large enough so that the binding moieties are able to bind with most if not all of the contaminants in the sample, but not so large that most of the target protein also are bound to the binding moieties.

It is an object of the present invention to provide methods for purifying a protein of interest. In one embodiment of the present invention, a method for purifying a target protein group is provided. This method comprises the steps of (a) contacting a sample comprising at least 95% of the target protein group and at most 5% of contaminating proteins with a library having at least 100 different binding moieties in an amount sufficient to bind contaminating proteins and a minority of the target protein group; (b) binding the contaminating proteins and the minority of the target protein group to the library of binding moieties; (c) separating the unbound target protein group from the contaminating proteins and target protein group bound to the library of binding moieties; and (d) collecting the unbound target protein group from the sample. The collected target protein group is more pure than the target protein group in the sample. In a preferred embodiment, the amount of the library of binding moieties is sufficient to bind a majority of the contaminating proteins.

In a preferred embodiment of the present invention, the sample comprises at least 98% of the target protein group and at most 2% of contaminating proteins.

In another preferred embodiment, the sample comprises a fermentation broth.

In a preferred embodiment of the present invention, the target protein group consists of a single protein species.

In a preferred embodiment of the present invention, the target protein comprises a naturally occurring protein. In another embodiment of the present invention, the target protein group comprises a recombinant protein. In a preferred embodiment, the recombinant protein is selected from the group consisting of an enzyme, a hormone, a growth factor, a receptor, a vaccine, an immunoglobulin and fragments of any of the foregoing. In another preferred embodiment of the present invention, the recombinant protein is selected from the group consisting of vascular endothelial growth factor (VEGF), platelet-derived growth factor (PDGF), fibroblast growth factor (FGF), epidermal growth factor (EGF), transforming growth factor (TGF), insulin-like growth factor (IGF), erythropoietin (EPO), bone morphogenetic protein (BMP), bone-derived neurotrophic factor (BDNF), colony stimulating factor (CSF), nerve growth factor (NGF), human growth hormone (hGH), tumor necrosis factor (TNF), insulin, tissue-type plasminogen activator (t-PA), interferon, interleukin (IL) and herceptin.

In other embodiments of the present invention, the library comprises at least 1,000, at least 10,000, at least 100,000, at least 1,000,000, at least 10,000,000, or at least 100,000,000 different binding moieties.

In a preferred embodiment of the present invention, the library is a non-selective library selected from the group consisting of a germ line antibody library, a phage display library of recombinant polypeptides, a dye library, a non-combinatorial library, a combinatorial library and portions of any of the foregoing. A preferred library comprises at least a portion of a combinatorial library. Also preferred is a combinatorial library comprising binding moieties selected from the group consisting of polypeptides, polynucleotides, lipids, oligosaccharides and small organic molecules. In another embodiment, the combinatorial library is a combinatorial library of hexapeptides.

Preferred binding moieties comprise bio-organic polymers. Binding moieties are selected from the group consisting of dyes, polypeptides, antibodies, nucleic acids, aptamers and small organic molecules.

The binding moieties can be bound to a solid support or supports. A preferred support or supports is a collection of beads or particles. The solid support or supports can be selected from the group consisting of discrete particles (spherical or irregular), beads, fibers, filters, membranes and monoliths. Each binding moiety can be attached to a different solid support. In another preferred embodiment, a plurality of different binding moieties are attached to a single solid support.

In another embodiment, the method of the present invention comprises, before step (a), the step of culturing a cell that produces the target protein group. The cell can be a eukaryotic cell or a prokaryotic cell. The target protein group can be purified from various samples. In one embodiment of the present invention, the sample is a cell supernatant. In yet another embodiment, the sample is a cell extract.

In one embodiment of the present invention, the method further comprises, before step (a), the steps of (i) subjecting a prior sample comprising less than 95% of the target protein group and more than 5% of the contaminating proteins to at least one purification step and (ii) collecting the sample comprising at least 95% of the target protein group and at most 5% of the contaminating proteins.

In one embodiment of the present invention, the method further comprises the step of (e) preparing a pharmaceutical composition by combining the collected target protein group with a pharmaceutically acceptable carrier.

According to the methods of the present invention, contacting a sample with a library of binding moieties can be done in multiple ways. In a preferred embodiment this step is done in a suspension batch process. In another preferred embodiment of the present invention, contacting a sample with a library of binding moieties is done by passing the sample over a column packed with the library of binding moieties attached to a solid support. In yet another preferred embodiment, contacting a sample with a library of binding moieties comprises a fluidized bed process.

It is also an object of the present invention to provide pharmaceutical compositions comprising a target protein group prepared according to the method of this invention and a pharmaceutically acceptable carrier. In a preferred embodiment, the target protein group is selected from the group consisting of an enzyme, a hormone, a growth factor, a receptor, a vaccine, an immunoglobulin and fragments of any of the foregoing. In another preferred embodiment of the present invention, the target protein group is selected from the group consisting of vascular endothelial growth factor (VEGF), platelet-derived growth factor (PDGF), fibroblast growth factor (FGF), epidermal growth factor (EGF), transforming growth factor (TGF), insulin-like growth factor (IGF), erythropoietin (EPO), bone morphogenetic protein (BMP), bone-derived neurotrophic factor (BDNF), colony stimulating factor (CSF), nerve growth factor (NGF), human growth hormone (hGH), tumor necrosis factor (TNF), insulin, tissue-type plasminogen activator (t-PA), interferon, interleukin (IL) and herceptin.

The present invention also provides kits for purifying a target protein group. In a preferred embodiment, the kit comprises (i) a library of binding moieties having at least 100 different binding moieties and (ii) an instruction to purify the target protein group by contacting a sample comprising at least 95% of the target protein group and at most 5% of contaminating proteins with the library of binding moieties. The kits of the present invention may further comprise a plurality of containers retaining incubation buffers for contacting the sample with the library of binding moieties or a fractionating column.

Additional kit embodiments of the present invention include optional functional components that would allow one of ordinary skill in the art to perform any of the method variations described herein.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Binding moiety" refers to a chemical moiety that binds an analyte.

"Library of binding moieties" refers to collection of different binding moieties.

"Antibody library" refers to a set of antibodies, i.e., a molecule able to bind to a specific epitope on an antigen and structurally defined as comprising an amino acid sequence that is recognized by one of skill as being derived from the framework region of an immunoglobulin encoding gene. Structurally, the simplest naturally occurring antibody (e.g., IgG) comprises four polypeptides chains, two copies of a heavy (H) chain and two copies of a light (L) chain, all covalently linked by disulfide bonds. Specificity of binding is found in the variable (V) determinant of the H and L chains. Regions of the antibodies that are primarily structural are constant (C). The term "antibody" includes whole antibody, functional fragments, modifications or derivatives of the antibody. It can also be a genetically manipulated product, or bispecific antibody or chimeric antibody, such as a humanized antibody. Antibodies may exist in a variety of forms including, for example, $F_V$ (consisting of the $V_L$ and $V_H$ domains of a single arm of an antibody), Fd (consisting of the $V_H$ and $C_{H1}$ domains), a dAB fragment (consisting of a $V_H$ domain; Ward et al., Nature, 341:544-546, 1989), an isolated complementary determining region (CDR), Fab (consisting of the $V_L$, $V_H$, $C_L$, and $C_{H1}$ domains, and $F(ab)_2$ (a bivalent fragment comprising two Fab fragments linked by a disulfide bridge at the hinge region) as well as in single chains. Single-chain antibodies (SCA), in which genes for a heavy chain and a light chain are combined into a single coding sequence, may also be used. Some SCA are genetically engineered molecules containing the variable region of the light chain, the variable region of the heavy chain, linked by a suitable polypeptide linker.

"Prior sample" refers to a potion or mixture of proteins comprising less than 95% of a target protein group of interest. Preferred prior samples include, but are not limited to, for example, fermentation broth, cell supernatants, cell extracts, animal extracts, and plant extracts.

The terms "protein," "polypeptide" and "peptide" as used herein refer to a polymer of amino acid residues. The terms also apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. Peptides and proteins of the present invention include amino acid polymers having D-and L-isoforms of individual amino acid residues, as well as other amino acid variants. Peptides are distinguished by the number of amino acid residues making up the primary structure of the molecule. For purpose of this invention, typically, peptides are those molecules comprising up to 50 amino acid residues and proteins comprise more than 50 amino acid residues.

"Purifying" a target protein group from a sample comprising the target protein group and one or more contaminating proteins or impurities refers to increasing the degree of purity of the target protein group by removing partially or completely at least one or more of the contaminating proteins or impurities.

"Recombinant protein" refers to a protein which has been produced in a host cell which has been transformed or transfected with nucleic acid encoding the protein, or produces the protein as a result of homologous recombination.

"Sample" refers to any composition, preferably an aqueous solution that comprises a target protein group of interest and contaminating proteins and is in a physical state which allows any target protein group of interest and any contaminating protein present in the sample to be contacted with a library of binding moieties. Samples may be of any source that comprises at least 95% of a target protein group of interest and at most 5% of contaminating proteins.

"Solid support" refers to any insoluble material including particles (e.g., beads), fibers, monoliths, membranes, filters, plastic strips and the like.

It is recognized that a protein can exist in a sample in several forms that can be co-purified. "Target protein group" refers to a single protein or group of related proteins to be purified. These related forms can result from either, or both, of pre-and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "a target protein group." Thus, for example, albumin and modified forms of albumin found in serum are a target protein group. Furthermore, a protein may be expressed as a multimeric protein, such as a dimeric protein. Examples of this are immunoglobulins and insulin. The term "target protein group" embraces this as well.

DETAILED DESCRIPTION OF THE INVENTION

Figure 1:
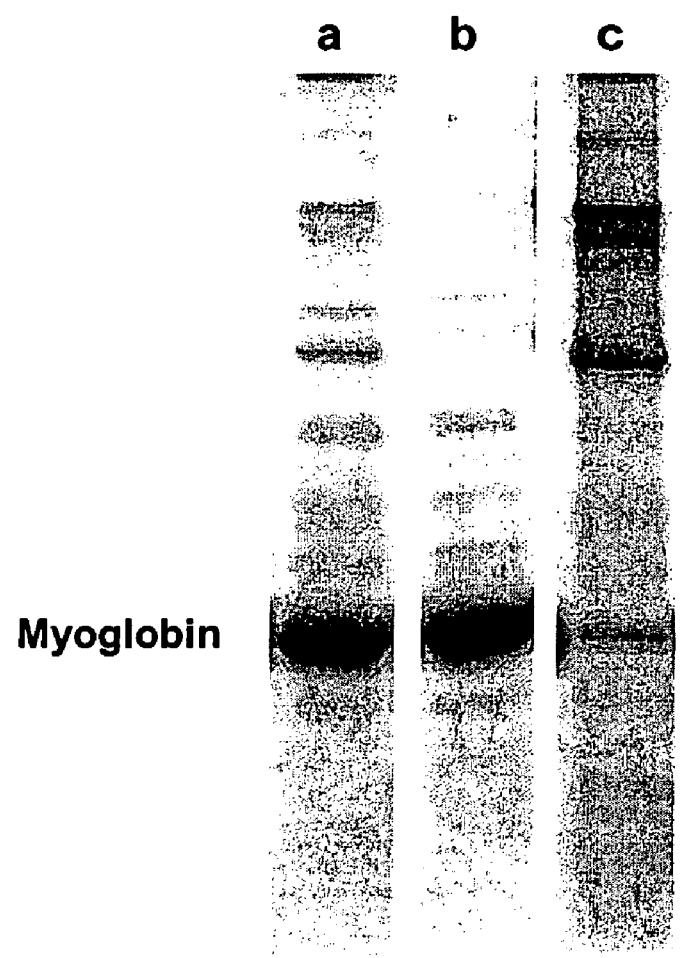
FIG. 1 shows the purification of a target group protein (myoglobin, contaminated with serum proteins) using a combinatorial peptide library and the methods of this invention. An SDS-PAGE shows the following protein fractions: lane "a": myoglobin contaminated with serum proteins; lane "b": polished myoglobin collected in the flowthrough; lane "c": contaminating proteins, including a minority of the myoglobin bound to the combinatorial peptide library.

The present invention provides methods and kits that allow one of ordinary skill in the art to purify a target protein group consisting of no more than 5 individual proteins, and preferably a single protein, from a sample comprising the target protein group and unknown contaminating proteins. The present invention further provides pharmaceutical compositions comprising a target protein group prepared according to methods of the invention. The invention also provides kits comprising components that would allow one of ordinary skill in the art to perform any of the methods described herein.

I. Purifying a Target Protein Group

The general principle of the methods of the present invention is based on the assumption that a library of binding moieties, such as a combinatorial library, comprises individual binding moieties that, together, can bind a wide array of analytes, in particular, a wide array of protein contaminants in a sample.

In a preferred embodiment of this invention, the number of individual binding moieties within a library of binding moieties, for example, a combinatorial library, is so large that it is assumed that each protein present in a sample has an affinity to at least one of the individual binding moieties. Typically, the binding moieties are attached to a solid support, such as beads. When a sample comprising a target protein group of interest that is being purified and a number of contaminating proteins is contacted with such a combinatorial library, individual binding moiety binds to a protein binding partner, including the target protein group and contaminating proteins. The large diversity of the combinatorial library provides binding moieties specific for every protein in a sample, i.e., for the target protein group of interest and the contaminating proteins. However, due to the limited capacity of the beads for a single protein species, minimal amounts of the target protein group will be bound and subsequently be removed from the sample. In theory, if the amount of a diverse combinatorial library attached to beads added to the sample is well calculated, virtually all contaminating proteins should be removed while the target protein group of interest will be very partially removed. The unbound target protein group of interest will remain in the supernatant and can be separated from the proteins bound to the library of binding moieties by filtration, centrifugation or other means. After the separation, the target protein group is collected. The collected target protein group is more pure than the target protein group in the sample.

While it is advantageous to purify a target protein group from a sample comprising the target protein group of interest and contaminating proteins, a skilled artisan will also appreciate that the methods of the invention may also be practiced to purify a target protein group of interest from a sample comprising the target protein group and non-polypeptide contaminants or impurities.

A. Target Protein Group and Contaminating Proteins

The methods and kits of the present invention are particularly useful for the purification of a target protein group from a sample comprising the target protein group and contaminating proteins.

In a preferred embodiment of the present invention, the target protein consists of a single protein species.

1. Target Protein Group

In one embodiment of the present invention, the target protein group, which is purified, comprises a recombinant protein. In a preferred embodiment of the present invention, the recombinant protein is selected from the group consisting of an enzyme, a hormone, a growth factor, a receptor, a vaccine, an immunoglobulin and fragments of any of the foregoing.

Target protein groups of interest also may be cellular proteins that are normally present in an animal or human and whose loss or malfunction is associated with a disease or infectious state such as a cancer, a viral infection, a parasite infection, a bacterial infection and the like. Of particular interest are also markers for cellular stress. Target protein groups indicating that an animal or human is under stress are an early indicator of a number of disease states, including certain mental illnesses, myocardial infarction and infection.

In yet another embodiment of the present invention, the target protein group comprises a therapeutic protein. A "therapeutic protein" is any protein, which is administered to a patient suffering from a disease to elicit a response that at least partially arrests or slows the symptoms or complications of the disease. Typically, a therapeutic protein is made recombinantly, i.e., it is a recombinant protein.

In another preferred embodiment of the present invention, the recombinant protein is selected from the group consisting of vascular endothelial growth factor (VEGF), platelet-derived growth factor (PDGF), fibroblast growth factor (FGF), epidermal growth factor (EGF), transforming growth factor (TGF), insulin-like growth factor (IGF), erythropoietin (EPO), bone morphogenetic protein (BMP), bone-derived neurotrophic factor (BDNF), colony stimulating factor (CSF), nerve growth factor (NGF), human growth hormone (hGH), tumor necrosis factor (TNF), insulin, tissue-type plasminogen activator (t-PA), interferon, interleukin (IL) and herceptin.

The therapeutic protein may be an antibody, such as IgA, IgD, IgE, IgG or IgM. The antibody may be monoclonal or polyclonal. The methods of the present invention are suitable for the purification of murine, chimeric and humanized antibodies.

The methods of the present invention are suitable to purify a variety of target protein groups, including, but not limited to, for example, (i) clotting factors, such as antithrombin III, coagulation factor VIIa, coagulation factor VIII, and coagulation factor IX; (ii) anti-coagulants, such as tissue plasminogen activators, streptokinase and urokinase; (iii) enzymes for rare congenital diseases, such as beta glucocerebrosidase, alpha-D-galactosidase, alpha-galactosidase A, alpha L-iduronidase, alpha-1,4-glucosidase, arylsulfutase B, iduronate-2-sulfatase, adenosine deaminase, human deoxyribonuclease I (hDNase-I), and human activated protein; (iv) insulin and genetically modified insulin; (v) reproductive hormones, such as human follicle-stimulating hormone, chorionic gonadotropin, and luteinizing hormone; (vi) other hormones, such as human growth hormone (Somatotropin), human bone morphogenetic protein 2, nesiritide, and parathyroid hormone; (vii) growth factors, such as erythropoietin (including Erythropoietin alfa, Erythropoietin beta, Darbepoetin alfa), keratinocyte growth factor, keratinocyte growth factor-2, granulocyte colony-stimulating factor (G-CSF) and granulocyte-macrophage colony-stimulating factor (Gm-CSF); (iix) interferons, such as alpha interferon (including pegylated alpha interferon and ribavirin, pegylated interferon alpha-2a and copegus), beta interferon (e.g., interferon beta-1a, interferon beta 1b), and gamma interferon; (ix) interleukins, such as IL-1 antagonists, IL-2, interleukin-10, interleukin-11, and interleukin-12; (x) monoclonal antibodies targeting leukocyte receptors, such as alpha 4 integrin antagonists, anti-thymocyte globulin, CD2 antagonists, CD3 antagonists, CD4 antagonists, CD11a antagonists (e.g., efalizumab), CD20 antagonists (Rituxan, Tiuxetan, Zeevalin, Bexxar), CD22 antagonists, CD33 antagonists (gemtuzumab ozogamicin), and CD52 antagonists (alemtuzumab); (xi) monoclonal antibodies targeting cytokines, such as chemokine antagonists, IL-2 antagonists, IL-4 antagonists, Il-5 antagonists, IL-6 antagonists, IL-12 antagonists, selectin antagonists, TNF-alpha antagonists; (xii) monoclonal antibodies targeting receptors on cancer cells, such as EGFR antagonists, HER-2 antagonists (e.g., herceptin), MUC-1 antagonists, VEGF antagonists; (xiiv) other antibodies, such as rituximab (humanized MAb), complement antibodies (e.g., C5 inhibitors), glycoprotein (GP) IIb/IIIa antagonists, IgE antagonists (e.g., omalizumab) and respiratory syncytial virus F-protein antagonists, Infliximab (chimaeric MAb), Adalimumab, and etanercept (fusion protein of antibody-Fc and p75-TNF receptor protein); (xiv) protein based drugs for treatment of non-Hodgkin's lymphoma, such as CD20 antagonists, CD22 antagonists and IL-2 antagonists; (xv) protein based drugs for treatment of leukemia, such as CD33 antagonists, CD52 antagonists, and alpha interferon; (xvi) protein based drugs for treatment of solid tumors, such as monoclonal antibodies trastuzumab (herceptin; humanised anti-HER-2 MAb; breast cancer), cetuximab and bevacizumab (EGFR and VEGR inhibitors), pemtumomab and oregovomab (MUC-1 inhiboitors); (xvii) protein therapeutic for the treatment of anemia, such as erythropoietin; (xiix) proteins for the treatment of congestive heart failure, such as nesiritide; (xix) proteins for the treatment of heart attack and stroke, such as alteplase, streptokinase, urokinase, GPIIb/IIIa receptor inhibitors and complement inhibitors; (xx) proteins for the treatment of hemophilia and von Willebrand's disease, such as coagulation factor VIII, coagulation factor IX, coagulation factor VII, and van Willebrand's factor; (xxi) proteins for the treatment of neutropenia, such as G-CSF, G-CSF-PEG conjugate, and Gm-CSF; (xxii) proteins for the treatment of thrompcytopenia, such as thrombopoietin; and (xxiiv) protein drugs for the treatment of pulmonary disease (for example, cystic fibrosis, emphysema, idiopathic pulmonary fibrosis), infectious disease (for example, hepatitis B (including envelope protein of the hepatitis B virus), hepatitis C, sepsis and RSV), immune disease (for example, asthma, rheumatoid arthritis, multiple sclerosis, acute transplant rejection, Crohn's disease and ulcerative colitis, psoriasis (e.g., alefacept), psoriatic arthritis and SCID), skin and bone disease (bone fractures, osteoporosis and wound) and other disease (for example, lysosomal storage disease, infertility (e.g., follitropin alpha), and diabetes) and fragments, chimeric proteins or fusion proteins of any of the above-listed proteins.

Other target protein groups of biological relevance that can be purified according to the methods of the present invention include renin; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; anti-clotting factors such as Protein C; atrial natriuretic factor; lung surfactant; a plasminogen activator, such human urine or tissue-type plasminogen activator (t-PA); bombesin; thrombin; hemopoietic growth factor; tumor necrosis factor-alpha and -beta; enkephalinase; RANTES; human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as EGFR, HER2, HER3 or HER4 receptor; and fragments, chimeric proteins or fusion proteins of any of the above-listed proteins.

In addition, specific target protein groups of interest include antibodies. A list of preferred antibodies is found in U.S. Patent Application No. 2003/0036095 (Tchaga), incorporated herein by reference in its entirety.

2. Contaminating Proteins

Typically, samples contain a target protein group of interest and contaminating proteins, which are proteins other than the target protein group that one desires to eliminate from the sample. The contaminating proteins may be of any number of individual proteins. However, in a preferred embodiment of the present invention, the concentration of contaminating proteins in a sample is at most 5%. In another preferred embodiment of the present invention, the concentration of contaminating proteins in a sample is at most 2%.

Because the methods and kits of the present invention provide library of binding moieties, one does not need any information of the identity or source of the contaminating proteins. In case where the target protein group is produced recombinantly in a host cell, the contaminating proteins, typically, are either from the host cell that produces the target protein group or from the cell culture medium used to grow the host cells. They can be of various category such as cytosol proteins, structural proteins, nuclear proteins, membrane proteins, enzymes and in particular proteases. Suitable host cells for producing a recombinant target protein group include animal cells, plant cells, insect cells, yeast and prokaryotic cells. One also can use cell free systems.

Preferred eukaryotic host cells for producing a recombinant target protein group or individual proteins of a target protein group include, but are not limited to, for example, vertebrate cells such as Chinese Hamster Ovary (CHO) cells, Baby Hamster Kidney (BHK) cells, monkey kidney CV1 cells (e.g., COS 7 cells), myeloma cells, human embryonic kidney cells (293 cells or 293 cells subcloned for growth in suspension culture), human cervical carcinoma cells (HELA), human lung cells (e.g., W138), human liver cells (e.g., Hep G2), 3T3 cells, mouse sertoli cells (e.g., TM4), African green monkey kidney cells (e.g., VERO-76), canine kidney cells (e.g., MDCK), buffalo rat liver cells (e.g., BRL 3A). Preferred are CHO and BHK cells. Accordingly, contaminating proteins present in a sample derived from CHO or BHK cells comprise CHO cell proteins or BHK cell proteins.

Other eukaryotic host cells useful for expressing a recombinant target protein group or individual proteins of a target protein group are yeast cells (e.g., *Saccharomyces cerevisiae, Schizosacharomyces pombe, Kluyveromyces lactis, Kluyveromyces fragiles, Kluyveromyces bulgaricus, Kluyveromyces wickeramii, Kluyveromyces waltii, Kluyveromyces drsophilarum, Kluyveromyces thermotolerans, Kluyveromyces marxianus, Pichia pastoris, Neurospora crassa*) transformed with recombinant yeast expression vectors. Also suitable purification according to the methods of the invention are target protein groups expressed in insect cells (e.g., *Spodoptera frugiperda, Aedes aegypti, Aedes albopictus, Drosophila melanogaster*, and *Bombyx mori*) transfected with recombinant viral expression vectors. Target protein groups expressed in plant cells can also be purified practicing the methods of the invention.

Preferred prokaryotic host cells for producing a recombinant target protein group or individual proteins of a target protein group include, but are not limited to, for example, *E. coli* (e.g., *E. coli* 294, *E. coli* B, *E. coli* X1776 *E. coli* W3110), *Enterobacter, Erwinia, Klebsiella, Proteus, Salmonella* (e.g., *Salmonella typhimurium*), *Serratia* (e.g., *Serratia marcescans*), *Shigella, Bacilli* (e.g., *B. subtilis, B. licheniformis*), *Pseudomonas* (e.g., *P. aeruginosa*), and *Streptomyces*. Preferred prokaryotic cells are *E. coli* and *B. subtilis*. Accordingly, contaminating proteins present in a sample derived from *E. coli* or *B. subtilis* comprise *E. coli* cell proteins or *B. subtilis* cell proteins.

B. Suitable Samples

A sample comprises at least 95% of a target protein group and at most 5% of contaminating proteins, also referred to herein as analytes. In samples wherein the target protein group comprises more than one individual protein, the combined total of the target protein group present in the sample is at least 95%. For example, when three individual proteins of interest (i.e., the target protein group) are present in a sample, the first individual protein may be present at at least 25%, the second individual protein may be present at at least 30% and the third individual protein may be present at at least 40%. In another preferred embodiment of the present invention, the sample comprises at least 98% of the target protein group and at most 2% of contaminating proteins.

Suitable samples for use in the present invention include gases, powders, liquids, suspensions, emulsions, permeable or pulverized solids, and the like. Preferably, a sample is a liquid. Most preferred samples are aqueous solutions. Samples may be taken directly from a source and used in the methods of the present invention without any preliminary manipulation. Preferred samples include, but are not limited to, for example, cell supernatant and cell extract.

When the expressed target protein group is secreted, it may be purified from the growth media or cell supernatant. Accordingly, in a preferred embodiment of the present invention, the sample from which a target protein is purified according to the invention, is a cell supernatant.

The methods of the invention can also be applied to a target protein group that is not secreted, i.e., a target protein group that once expressed in a host cell remains in the host cell from where it will be purified. When the expressed target protein group is not secreted from the host cell, the host cell is preferably disrupted and the target protein group is released into an aqueous extract. In another preferred embodiment of the present invention, the sample from which a target protein is purified according to the invention, is a cell extract.

Alternatively, a prior sample, comprising less than 95% of a target protein group of interest, is manipulated in a variety of ways as described further below, to enhance its property and to obtain a sample comprising at least 95% of the target protein group.

A prior sample may be a biological sample taken from biological sources including biological fluids such as whole blood and blood-derivatives, serum, plasma, urine, prostate fluid, tears, oral fluid, saliva, semen, seminal fluid, mucus, stool, sputum, cerebrospinal fluid, bone marrow, lymphatic fluid, fetal fluid, amniotic fluid, milk, and sweat. A prior sample also includes biological tissue specimen, cell extracts, fermentation broth, and cell supernatants. Biological samples may be collected by swabbing, scraping, withdrawing surgically or with a hypodermic needle, and the like. The collection method in each instance is highly dependent upon the biological source and the situation, with many alternative suitable techniques of collection well-known to those of skill in the art. Often, a target protein from a fermentation broth or from a biological fluid can be purified to about at least 95% by classical fractionation and purification methods, such as filtration, precipitation, chromatography or electrokinetic methods.

Often, a target protein group, once expressed in a host cell, is secreted into the cell culture medium from where it may be purified. Accordingly, a prior sample can be a fermentation broth. Typically, a fermentation broth comprises host cells expressing the target protein group, cellular debris and particulate matter. A prior sample may be a fermentation broth that has been subjected to, e.g., a pH adjustment, an ionic strength adjustment, a temperature adjustment, a water dilution and/or one or more solid/liquid separatory techniques such as flocculation, centrifugation, filtration or micro filtration. Thus, the fermentation broth may be further clarified by removing the host cells expressing the target protein group, cellular debris and particulate matter. The target protein group present in the fermentation broth or in the clarified fermentation broth may be further concentrated before applying the methods of the present invention. However, clarification and/or concentration are not required steps.

C. Suitable Binding Moieties

The method of purifying a target protein group comprises the step of contacting a sample comprising at least 95% of the target protein group and at most 5% of contaminating proteins with a library of binding moieties having at least 100 different binding moieties in an amount sufficient to bind a contaminating proteins and a minority of the target protein group.

A library of binding moieties used in this invention comprises at least 100 different binding moieties. Preferably, the library of binding moieties includes at least as many different binding moieties as there are analytes in the sample. Thus, ideally a library of binding moieties comprises at least 10, 50, 100, 1,000, 10,000, 100,000, 1,000,000, 3,000,000, 10,000,000, 1,000,000,000 binding moieties. Preferably, each binding moiety recognizes a different analyte.

Binding moieties may also be soluble combinatorial molecules. Soluble combinatorial molecules preferably comprise a linker moiety. A "linker moiety" allows the binding moiety to be coupled to a complementary solid support comprising a complementary linker moiety. Soluble combinatorial molecules are typically contacted to a sample and allowed to bind analyte(s) of interest prior to isolating the resulting complexes by binding or coupling the combinatorial molecules via their linker moiety to a solid support. Alternatively, the combinatorial molecules can be coupled to a solid support prior to contacting the sample.

Library of binding moieties may exist and interact with analytes detectable using the present invention in any physical state compatible with formation of molecular interactions, including gaseous, aqueous and organic suspensions and emulsions and, most preferably in a liquid state.

Typically, and as described in detail below, library of binding moieties are coupled to an insoluble solid support or particulate material. Each solid support or insoluble particle preferably carries several copies of the same binding moiety, with each particle type coupling a different binding moiety.

Library of binding moieties of the present invention may be produced using any technique known to those of skill in the art. For example, library of binding moieties may be chemically synthesized, harvested from a natural source or, in the case of library of binding moieties that are bio-organic polymers, produced using recombinant techniques.

Binding moieties may be purchased pre-coupled to the solid supports, or may be indirectly attached or directly immobilized on the solid support using standard methods (see, for example, Harlow and Lane, *Antibodies*, Cold Spring Harbor Laboratory, Cold Spring Harbor, N.Y. (1988); Biancala et al., Letters in Peptide Science 2000, 7(291):297; MacBeath et al., Science 2000, 289:1760-1763; Cass et al., ed., *Proceedings of the Thirteenth American Peptide Symposium*; Leiden, Escom, 975-979 (1994); U.S. Pat. No. 5,576,220; Cook et al., Tetrahedron Letters 1994, 35:6777-6780; and Fodor et al., Science 1991, 251(4995):767-773).

1. Combinatorial Libraries

In one embodiment of this invention the library of binding moieties is a combinatorial library or portion thereof. A combinatorial chemical library is a collection of compounds generated by either chemical synthesis or biological synthesis, by combining a number of chemical "building blocks" in all possible combinations. For example, a complete linear combinatorial chemical library, such as a polypeptide library, is formed by combining a set of chemical building blocks (amino acids) in every possible way for a given compound length (i.e., the number of amino acids in a polypeptide compound). As an example, if the number of building blocks is 5 and the construct is composed of five members, the number of possible linear combinations is of $5^5$ or 3,125 members. In this case the building blocks (A, B, C, D and E) are assembled linearly such as: A-A-A-A-A; A-A-A-A-B; A-A-A-A-C; A-A-A-B-A; A-A-A-B-B; A-A-A-B-C; . . . ; A-A-B-A-A; A-A-B-A-B; A-A-B-A-C; . . . ; E-E-E-E-C; E-E-E-E-D; E-E-E-E-E.

Another form of combinatorial library is scaffold-based. These constructs are based of a single central molecule or core, comprising positions that can be selectively substituted by building blocks. An example is given by trichloro-triazine (three substitutable positions) on which several substituents can be attached. If the number of substituents is three, the number of possible combinations is 10. It is also possible to consider the relative positioning of each substituent; in this case the number of combinations is larger.

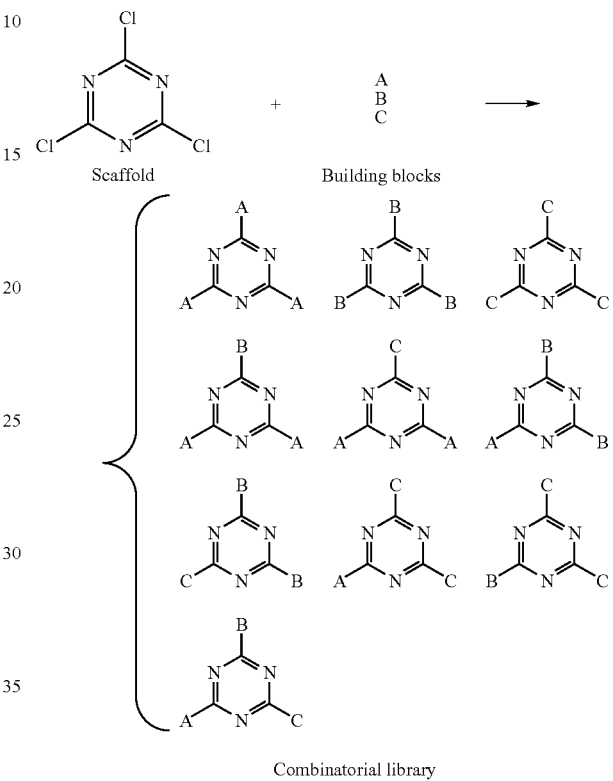

Combinatorial library

As a third level it is possible to combine linear combinatorial libraries with scaffold-based libraries where substituents of this latter are combinatorial linear sequences.

Millions of chemical compounds can be synthesized through such combinatorial mixing of chemical building blocks. For peptide binding moieties, the length is preferably limited to 15, 10, 8, 6 or 4 amino acids. Nucleic acid binding moieties of the invention have preferred lengths of at least 4, more preferably 6, 8, 10, 15, or at least 20 nucleotides. Oligosaccharides are preferably at least 5 monosaccharide units in length, more preferably 8, 10, 15, 20, 25 or more monosaccharide units.

Combinatorial libraries may be complete or incomplete. Complete combinatorial libraries of biopolymers are those libraries containing a representative of every possible permutation of monomers for a given polymer length and composition. Incomplete libraries are those libraries lacking one or more possible permutation of monomers for a given polymer length.

Peptide binding moieties are a preferred embodiment of the claimed invention. Methods for generating libraries of peptide binding moieties suitable for use in the claimed invention are well known to those of skill in the art, e.g., the "split, couple, and recombine" method (see, e.g., Furka et al., Int. J. Peptide Protein Res., 37: 487-493 (1991); Houghton et al., Nature 354:84-88 (1991); Lam et al., Nature, 354: 82-84 (1991); International Patent Application WO 92/00091; and U.S. Pat. Nos. 5,010,175, 5,133,866, and 5,498,538) or other approaches known in the art. The expression of peptide libraries also is described in Devlin et al., Science, 249: 404-406 (1990).

Combinatorial and synthetic chemistry techniques well-known in the art can generate libraries containing millions of members (Lam et al., Nature 354: 82-84 (1991) and International (PCT) Patent Application WO 92/00091), each having a unique structure. A library of linear hexamer ligands made with 18 of the natural amino acids, for example, contains $34 \times 10^6$ different structures. When amino acid analogs and isomers are also included, the number of potential structures is practically limitless. Moreover, each member of such a library potentially possesses the capacity to bind to a different molecule. Members of a combinatorial library can be synthesized on or coupled to a solid support, such as a bead, with each bead essentially having millions of copies of a library member on its surface. As different beads may be coupled to different library members and the total number of beads used to couple the library members large, the potential number of different molecules capable of binding to the bead-coupled library members is enormous.

Hammond et al., U.S. 2003/0212253 (Nov. 13, 2003) describes combinatorial libraries along the following lines. Peptide binding moiety libraries may be synthesized from amino acids that provide increased stability relative to the natural amino acids. For example, cysteine, methionine and tryptophan may be omitted from the library and unnatural amino acids such as 2-naphylalanine and norleucine included. The N-terminal amino acid may be a D-isomer or may be acetylated to provide greater biochemical stability in the presence of amino-peptidases. The binding moiety density must be sufficient to provide sufficient binding for the target molecule, but not so high that the binding moieties interact with themselves rather than the target molecule. A binding moiety density of 0.1 μmole-500 μmole per gram of dry weight of support is desired and more preferably a binding moiety density of 10 μmole-100 μmole per gram of support is desired. A 6-mer peptide library was synthesized onto Toyopearl-AF Amino 650M resin (Tosohaas, Montgomeryville, Pa.). The size of the resin beads ranged from 60-130 mm per bead. Initial substitution of the starting resin was achieved by coupling of a mixture of Fmoc-Ala-OH and Boc-Ala-OH (1:3.8 molar ratio). After coupling, the Boc protecting group was removed with neat TFA in full. The resulting deprotected amino groups were then acetylated. Peptide chains were assembled via the remaining Fmoc-Ala-OH sites on the resin bead. Standard Fmoc synthetic strategies were employed. In one embodiment a typical experiment, six grams of Fmoc-Ala-(Ac-Ala-)Toyopearl Resin was deprotected with 20% piperdine/DMF (2×20 min), then washed with DMF (8 times) and equally divided into 18 separate reaction vessels. In each separate vessel, a single Fmoc-amino acid was coupled to the resin (BOP/NMM, 5-10 told excess) for 4-7 hours. The individual resins were washed and combined using the "split/mix" library technique (Furka et al., Int. J. Peptide Protein Res., 37, 487-493 (1991); Lam et al., Nature, 354, 82-84 (1991); International Patent Application WO 92/00091 (1992); U.S. Pat. No. 5,010,175; U.S. Pat. No. 5,133,866; and U.S. Pat. No. 5,498,538). The cycle of deprotection and coupling was repeated until the amino acid sequence was completed (six cycles for a hexamer library). The final Fmoc was removed from peptide resins using 20% piperidine/DMF in separate reaction vessels during the last coupling cycle. Side-chain protecting groups were removed with TFA treatment (TFA:H.sub.20:Phenol, 90:5:5) for 2 hours. Resins were washed extensively and dried under a vacuum. Peptide densities achieved were typically in the range of 0.06-0.12 mmol/g of resin.

Sequencing and peptide composition of peptide ligand-resin bead complexes were confirmed, and the degree of substitution of the resin was calculated by quantitative amino acid analysis at Commonwealth Biotechnologies, Inc., Richmond, Va. Sequencing was performed at Protein Technologies Laboratories, Texas A&M University, by Edman degradation using a Hewlett PackardG1005A.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

2. Small Organic Molecules

In a preferred embodiment of the present invention, the method comprises the step of contacting a sample with a library of binding moieties, wherein the library is a combinatorial library of small organic molecules.

Accordingly, small molecules are also contemplated as library of binding moieties for use in the methods and kits of the present invention. Typically, small organic molecules have properties that allow for ionic, hydrophobic or affinity interaction with an analyte. Libraries of small organic molecules include chemical groups traditionally used in chromatographic processes such as mono-, di-and tri-methyl amino ethyl groups, mono-, di-and tri-ethyl amino ethyl groups, sulphonyl, phosphoryl, phenyl, carboxymethyl groups and the like. For example libraries may use benzodiazepines, (see, e.g. Bunin et al., Proc Natl Acad Sci USA 1994, 91:4708-4712) and peptoids (e.g. Simon et al., Proc Natl Acad Sci USA 1992, 89:9367-9371). In another embodiment, the binding moiety is a dye or a triazine derivative. This list is by no means exhaustive, as one of skill in the art will readily recognize thousands of chemical functional groups with ionic, hydrophobic or affinity properties compatible with use as library of binding moieties in the methods of the present invention.

In a preferred embodiment of the present invention, the combinatorial library of small organic molecules is covalently attached to a solid support, preferably a plurality of beads. As described further herein, attachment of the combinatorial library of small organic molecules to the solid support can be direct or via a linker.

3. Biopolymers

In a preferred embodiment of the present invention, the method comprises the step of contacting a sample with a library of binding moieties, wherein the library is a combinatorial library of biopolymers.

In one embodiment of the present invention, biopolymers are selected from the group consisting of polypeptides, polynucleotides, lipids and oligosaccharides.

For biopolymer library of binding moieties of the present invention, linear length is preferably between 4 and 50 monomeric units, in particular no more than 15, no more than 10, desirably 8, 7, 6, 5, 4 or 3 monomeric units. For peptide libraries, the length is preferably limited to no more than 15, 10, 8, 6 or 4 amino acids. Nucleic acid libraries have preferred lengths of at least 4, more preferably at least 6, 8, 10, 15, or at least 20 nucleotides. Oligosaccharides are preferably at least 5 monosaccharide units in length, more preferably at least 8, 10, 15, 20, 25 or more monosaccharide units.

In one embodiment of the present invention, the biopolymers are covalently attached to a solid support, preferably a plurality of beads. As described further herein, attachment of the combinatorial library of biopolymers to the solid support can be direct or via a linker.

a) Peptides

In a preferred embodiment of the present invention, a biopolymer is a peptide. Particularly preferred library of binding moieties comprise peptides having no more than 50, 40, 30, 25, 20, 15, 10, 8, 6 or 4 amino acids, as they are easily produced using recombinant or solid phase chemistry techniques. Moreover, peptide library of binding moieties may be produced in a manner that eases their use for the methods of the present invention. For example, peptides may be recombinantly produced as a phage display library where the peptide is presented as part of the phage coat (see, e.g., Tang et al., J Biochem 1997, 122(4):686-690). In this context, the peptides would be attached to a solid support, the phage. Other methods for generating libraries of peptide binding moieties suitable for use in the claimed invention are also well known to those of skill in the art, e.g., the "split, couple, and recombine" method (see, e.g., Furka et al., Int J Peptide Protein Res 1991, 37:487-493; Fodor et al., Science 1991, 251:767-773; Houghton et al., Nature 1991, 354:84-88; Lam et al., Nature 1991, 354:82-84; International Patent Application WO 92/00091; and U.S. Pat. Nos. 5,010,175, 5,133,866, and 5,498,538, all of which herewith are incorporated in their entirety by reference) or other approaches known in the art. The expression of peptide libraries also is described in Devlin et al., Science 1990, 249:404-406.

Libraries of peptide binding moieties may be synthesized from amino acids that provide increased stability relative to the natural amino acids. For example, cysteine, methionine and tryptophan may be omitted from the library and unnatural amino acids such as 2-naphylalanine and norleucine included. The N-terminal amino acid may be a D-isomer or may be acetylated to provide greater biochemical stability in the presence of amino-peptidases. The library density must be sufficient to provide sufficient binding for an analyte, but not so high that the library of binding moieties interact with themselves rather than the analyte. A library density in the range of 0.1 μmole to 500 μmole per gram of dry weight of solid support is desired and more preferably a library density in the range of 10 μmole to 100 μmole per gram of solid support is desired. Other preferred ranges are 10 μmole to 100 μmole per ml of solid support.

In some combinatorial peptide library embodiments, the peptides are expressed on the surface of a recombinant bacteriophage to produce large libraries. Using the "phage method" (Scott and Smith, Science 249:386-390, 1990; Cwirla, et al., Proc. Natl. Acad. Sci., 87:6378-6382, 1990; Devlin et al., Science, 49:404-406, 1990), very large libraries can be constructed ($10^6$-$10^8$ chemical entities). A second approach uses primarily chemical methods, of which the Geysen method (Geysen et al., Molecular Immunology 23:709-715, 1986; Geysen et al., J. Immunologic Method 102:259-274, 1987; and the method of Fodor et al. (Science 251:767-773, 1991) are examples. Furka et al. (14th International Congress of Biochemistry, Volume #5, Abstract FR:013, 1988; Furka, Int. J. Peptide Protein Res. 37:487-493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In a preferred embodiment of the present invention, the method comprises the step of contacting a sample with a library of binding moieties, wherein the library of binding moieties comprises an antibody library antibody libraries (see, e.g., Vaughn et al., Nature Biotechnology 1996, 14(3): 309-314; PCT/US96/10287). In a preferred embodiment of the present invention, the method comprises the step of contacting a sample with an antibody library displayed on phage particles.

b) Polynucleotides

Nucleic acids are another preferred biopolymer library of binding moieties. As with peptides, nucleic acids may be produced using synthetic or recombinant techniques well-known to those of skill in the art. The terms "polynucleotide," "nucleic acid," and "nucleic acid molecule" are used interchangeably herein and refer to the polymeric form of deoxyribonucleotides, ribonucleotides, and/or their analogs in either single stranded form, or a double-stranded helix. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g., DNA or RNA, or may be synthetic analogs, as known in the art. Such analogs may be preferred for use as binding moieties because of superior stability. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Preferable nucleic acid binding moieties are at least 4, more preferably at least 6, 8, 10, 15, or 20 nucleotides in length. Nucleic acid binding moieties include double stranded DNA or single stranded RNA molecules (e.g., aptamers) that bind to specific molecular targets, such as a protein or metabolite.

(1) Oligosaccharides

A biopolymer can be an oligosaccharide. Thus, oligosaccharide binding moieties are also contemplated for use in the methods and kits of the invention. Oligosaccharide binding moieties are preferably at least 5 monosaccharide units in length, more preferably at least 8, 10, 15, 20, 25 or more monosaccharide units in length.

(2) Lipids

A biopolymer can be a lipid. As used herein, the term "lipid" refers to a hydrophobic or amphipathic moiety. Thus, lipid binding moieties are also contemplated for use in the methods and kits of the invention. Suitable lipids include a C14 to C50 aliphatic, aryl, arylalkyl, arylalkenyl, or arylalkynyl moiety, which may include at least one heteroatom selected from the group consisting of nitrogen, sulfur, oxygen, and phosphorus. Other suitable lipids include a phosphoglyceride, a glycosylglyceride, a sphingolipid, a sterol, a phosphatidyl ethanolamine or a phosphatidyl propanolamine. Lipid binding moieties are preferably at least 5 units in length, more preferably at least 8, 10, 15, 20, 25, 50 or more units in length.

D. Attachments of Binding Moieties to Solid Support

In a preferred embodiment of the present invention, the method comprises the step of contacting a sample with a library of binding moieties, wherein the library of binding moieties is attached to a solid support.

1. Solid Supports

Acceptable solid supports for use in the present invention can vary widely. A solid support can be porous or nonporous, but is preferably porous. It can be continuous or non-continuous, flexible or nonflexible. A solid support can be made of a variety of materials including ceramic, glassy, metallic, organic polymeric materials, or combinations thereof.

Preferred solid supports include organic polymeric supports, such as particulate or beaded supports, woven and nonwoven webs (such as fibrous webs), microporous fibers, microporous membranes, hollow fibers or tubes. Polyacrylamide and mineral supports such as silicates and metal oxides can also be used. Woven and nonwoven webs may have either regular or irregular physical configurations of surfaces. Particularly preferred embodiments include solid supports in the form of spherical or irregularly-shaped beads or particles.

Porous materials are useful because they provide large surface areas. The porous support can be synthetic or natural, organic or inorganic. Suitable solid supports with a porous structure have pores of a diameter of at least about 1.0 nanometer (nm) and a pore volume of at least about 0.1 cubic centimeter/gram ($cm^3/g$). Preferably, the pore diameter is at least about 30 nm because larger pores will be less restrictive to diffusion. Preferably, the pore volume is at least about 0.5 $cm^3/g$ for greater potential capacity due to greater surface area surrounding the pores. Preferred porous supports include particulate or beaded supports such as agarose, hydrophilic polyacrylates, polystyrene, mineral oxides and Sepharose, including spherical and irregular-shaped beads and particles.

For significant advantage, the solid supports for binding moieties are preferably hydrophilic. Preferably, the hydrophilic polymers are water swellable to allow for greater infiltration of analytes. Examples of such supports include natural polysaccharides such as cellulose, modified celluloses, agarose, cross-linked dextrans, amino-modified cross-linked dextrans, guar gums, modified guar gums, xanthan gums, locust bean gums and hydrogels. Other examples include cross-linked synthetic hydrophilic polymers such as polyacrylamide, polyacrylates, polyvinyl alcohol (PVA) and modified polyethylene glycols.

Another form of solid support is a phage as it is used in phage display libraries. A phage display library is formed from bacteriophage that has been recombinantly manipulated to express binding moieties as part of the phage protein coat. Using phage display, libraries of binding moieties may be easily constructed and used for the methods of the invention.

2. Microparticulate Solid Supports

A preferred embodiment of the present invention utilizes small, beaded, microparticulate solid supports that are less than 1000 μm, preferably less than 100, 10, 1 or 0.1 μm in diameter. Microparticulate solid supports are desirable because they possess increased surface area to volume ratio compared to the larger bead. Microparticulate solid supports also decrease the volume of support necessary to contain a combinatorial library, thereby allowing more complex and efficient libraries to be used. Using existing equipment however, it is difficult to synthesize combinatorial libraries on very small (<10 μm) beads due to the limitations in frit sizes of the filter systems used. To overcome this problem the combinatorial library may be synthesized in bulk on a bead that may then be fragmented by mechanically grinding, crushing, or sonicating to form a powder or collection of micro-particles. Using these techniques, microparticulate solid supports coupled to different binding moieties may be produced. These in turn may be extensively mixed to form a more uniform composition relative to mixing larger or various sizes of different beads.

Non-reacted cross-linking groups on the surface may be reacted with a small chemical such a mercapto-ethanol to prevent further reactivity. In addition, surfaces may be further treated to prevent non-specific adhesion of protein.

The microparticulate solid support may also be magnetic beads allowing for an easy one-step separation of unbound target protein group and proteins bound to the binding moieties coupled to the magnetic beads.

Eluted analytes (for example, minority of target protein group and contaminating proteins) may be analyzed for protein composition according to molecular weight by several methods, including mass spectrometry, SDS-PAGE, capillary electrophoresis, or by pI through isoelectric focusing.

Alternatively, the microparticulate solid supports may be compounded with a bulking agent and compacted into tablet form. In this format it may be added directly to a sample solution or instead, first suspended in buffer.

Microparticulate solid supports may be placed into solution such as agarose or acrylamide and cross-linked into a gel itself or cross-linked to each other through a polymerization reaction with a cross-linker on a fiber to form a monolithic material.

Alternatively microparticulate solid supports may be immobilized onto a thin film of adhesive.

Another approach is the entrapment of microparticulate solid supports in a porous matrix. Such matrixes could include nonwoven fibers or webs with the particles possibly being incorporated during the melt blowing stage.

Microparticles can be incorporated into a single sheet or stack of membranes as desired to achieve the appropriate desired binding capacity, in which the microparticulate solid supports are entrapped between the layers by calendaring or hydroentanglement.

The membrane composition can be selected from natural or synthetic sources including polyester and polypropylene fibers and meshes. Of course, one of skill in the art will be aware that many of the techniques described in this section are generally applicable to other embodiments of the present invention.

3. Coupling a Binding Moiety to a Solid Support

In a preferred embodiment of the present invention, binding moieties are coupled to one or more solid supports. Coupling of binding moieties to a solid support may be accomplished through a variety of mechanisms.

The solid support can be derivatized with a fully prepared library of binding moieties by attaching a previously prepared library of binding moieties to the solid support. Alternatively, the library of binding moieties may be formed on the solid support by attaching a precursor molecule to the solid support and subsequently adding additional precursor molecules to the growing chain bound to the solid support by the first precursor molecule. This mechanism of building the adsorbent on the solid support is particularly useful when the binding moiety is a polymer, particularly a biopolymer such as a polypeptide, polynucleotide or polysaccharide molecule. A biopolymer binding moieties can be provided by successively adding monomeric components (e.g., amino acids, nucleotides or simple sugars) to a first monomeric component attached to the solid support using methods known in the art. See, e.g., U.S. Pat. No. 5,445,934 (Fodor et al.), incorporated herewith in its entirety by reference.

As few as one and as many as 10, 100, 1,000, 10,000, 1,000,000, 3,000,000, 10,000,000, 1,000,000,000 or more binding moieties may be coupled to a single solid support. In preferred embodiments the solid support is in the form of beads, with a single, different, binding moiety type bound to each bead. For example in a peptide binding moiety library, peptides representing one possible permutation of amino acids would be bound to one bead, peptides representing another possible permutation to another bead, and so on.

Binding moieties may be coupled to a solid support using reversible or non-reversible reactions. For example, non-reversible reactions may be made using a support that includes at least one reactive functional group, such as a hydroxyl, carboxyl, sulfhydryl, or amino group that chemically binds to the binding moieties, optionally through a spacer group. Suitable functional groups include N-hydroxysuccinimide esters, sulfonyl esters, iodoacetyl groups, aldehydes, epoxy, imidazolyl carbamates, and cyanogen bromide and other halogen-activated supports. Such functional groups can be provided to a support by a variety of known techniques. For example, a glass surface can be derivatized with aminopropyl triethoxysilane in a known manner. In some embodiments, binding moieties are coupled to a solid support during synthesis, as is known to those of skill in the art (e.g., solid phase peptide and nucleic acid synthesis).

Alternatively, reversible interactions between a solid support and a binding moiety may be made using linker moieties associated with the solid support and/or the binding moieties. A variety of linker moieties suitable for use with the present invention are known, some of which are discussed herein. Use of linker moieties for coupling diverse agents is well known to one of ordinary skill in the art, who can apply this common knowledge to form solid support/binding moiety couplings suitable for use in the present invention with no more that routine experimentation.

In certain embodiments, each different binding moiety can be coupled to a different solid support. This is the case, for example, when a combinatorial library is built on beads using the split-pool-and-recombine method. Alternatively, a collection of binding moieties can be coupled to a pool of beads, so that each bead has a number of different binding moieties attached. This can be done, for example, by creating a combinatorial library on a first set of supports, cleaving the binding moieties from the supports and re-coupling them to a second collection of supports.

a) Linker Moieties

Coupling of a binding moiety to a solid support may also be accomplished for example, by using linker moieties. In this embodiment of the present invention, a sample is contacted with a binding moiety that includes a linker moiety that allows targeted and/or reversible coupling of the binding moiety to a solid support preferably a microparticulate solid support. A "linker moiety" allows the binding moiety to be coupled to a complementary solid support comprising a complementary linker moiety.

Exemplary linker moieties include epitope and his-tags, which are attached to a binding moiety, for example a peptide, to form a fusion protein. In these instances, a cleavable linker sequence, such as those specific for Factor XA or enterokinase (Invitrogen, San Diego, Calif.) may be optionally included between the peptide and the linker moiety to facilitate isolation and/or separation of the components of the fusion molecule. Protein domains specifically recognized by designer ligands may also be used as linker moieties (See, e.g., Deisenhofer, Biochemistry 20 (1981) 2361-2370). Many other equivalent linker moieties are known in the art. See, e.g., Hochuli, Chemische Industrie, 12:69-70 (1989); Hochuli, *Genetic Engineering, Principle and Methods,* 12:87-98 (1990), Plenum Press, N.Y.; and Crowe, et al. (1992) *QIAexpress: The High Level Expression & Protein Purification System,* QIAGEN, Inc. Chatsworth, Calif.; which are incorporated herein in their entirety by reference.

Antigenic determinants and other characteristic properties of the binding moieties to be coupled to a solid support may also serve as linker moiety tags. Exemplary linker moieties include poly-histidine (poly-his) or poly-histidine-glycine (poly-his-gly) tags; the flu HA tag polypeptide and its antibody 12CA5 (Field et al., Mol Cell Biol 1988, 8:2159-2165); the c-myc tag and the 8F9, 3C7, 6E10, G4, B7 and 9E10 antibodies thereto (Evan et al., Mol Cell Biol 1985, 5:3610-3616); and the Herpes Simplex virus glycoprotein D (gD) tag and its antibody (Paborsky et al., Protein Engineering 1990, 3(6):547-553). Other tag polypeptides include the Flag-peptide (Hopp et al., BioTechnology 1988, 6:1204-1210); the KT3 epitope peptide (Martin et al., Science 1992, 255:192-194); a α-tubulin epitope peptide (Skinner et al., J Biol Chem 1991, 266:15163-15166); and the T7 gene 10 protein peptide tag (Lutz-Freyermuth et al., Proc Natl Acad Sci USA 1990, 87:6393-6397).

E. Contacting a Sample with and Binding a Sample to a Library of Binding Moieties The present invention provides methods for purifying a target protein group. These methods comprise the steps of (a) contacting a sample comprising at least 95% of the target protein group and at most 5% of contaminating proteins with a library of binding moieties having at least 100 different binding moieties in an amount sufficient to bind contaminating proteins and a minority of the target protein group and (b) binding the contaminating proteins and the minority of the target protein group to the library of binding moieties.

When introduced to a sample containing a diversity of analytes, the binding moieties will bind various contaminants in the sample, such as contaminating proteins. Abundant analytes, such as the target protein group of interest, will be present in amounts far in excess of the amount necessary to saturate the capacity of their respective binding moieties. Therefore, a high percentage of the total amount of these abundant analytes will remain unbound and only a minority will bind to the binding moieties. Conversely, the lesser amounts of trace analytes, such as the contaminating proteins, means that these proteins will not saturate all of their available binding moieties. Therefore, the majority of the starting amount of the contaminating proteins will bind to their respective binding moieties.

Analytes, target protein groups and contaminating proteins, present in a sample are contacted with a library of binding moieties having at least 100 different binding moieties under conditions that allow each binding moiety to bind to its corresponding analyte if present in the sample. Generally, a sample is contacted with a library of binding moieties under conditions that allow binding of contaminating proteins and the minority of the target protein group to the binding moieties. The conditions under which a target protein group is purified will vary according to various parameters, including the inherent properties of the target protein group, the properties of the contaminating proteins, etc.

Contacting a sample with a library of binding moieties can be accomplished in a variety of ways. For example, contacting the library of binding moieties with the sample may be accomplished by admixing the two, swabbing the sample onto the library of binding moieties, flowing the sample over the solid support having binding moieties attached thereto, and other methods that would be obvious to those of ordinary skill in the art. In a preferred embodiment of the present invention, contacting a sample with a library of binding moieties is done in a suspension batch process. In another preferred embodiment of the present invention, contacting a sample with the library of binding moieties is accomplished by passing the sample over a column packed with the library of binding moieties attached to a solid support. In yet another preferred embodiment of the present invention, contacting a sample with a library of binding moieties comprises a fluidized bed process.

As inferred above, the binding moieties may contact the sample directly, or the binding moieties may be first attached to a solid support. By way of example, in one preferred embodiment, the binding moieties include a linker moiety. In this embodiment the binding moieties are contacted directly to the sample in a manner that allows analytes (i.e., target protein group and contaminating proteins) present in the sample to bind to the binding moieties. After sufficient time has elapsed, a solid support that includes a complementary linker moiety to the linker moiety of the binding moieties is contacted to the sample. This allows the binding moieties to couple with the solid support through the linker moiety, while retaining the captured analyte. For example, a binding moiety having a biotin linker moiety would couple to a solid support comprising avidin or streptavidin coupled to its surface.

In one embodiment of the present invention, the library of binding moieties is coupled to the solid support prior to contacting the sample. In this alternative embodiment, the solid support (with coupled binding moieties) is simply contacted with the sample for a time sufficient to allow the binding moieties to bind the analytes, then the solid support is withdrawn from the sample with the analytes bound to it via formation of a complex between the analytes and the binding moieties.

The binding moieties may be added directly to a sample comprising the target protein group and the contaminating proteins. Alternatively, any suitable binding buffer may be added for this purpose. Exemplary binding buffers include aqueous salt solutions of very low or high ionic strength, detergent solutions, and organic solvents as described further below. Solutions and suspensions of agents that competitively bind to binding moieties my also be used in binding buffers, provide that such competitive binding agents do not interfere with subsequent binding contaminating proteins and the minority of the target protein group. The binding buffer(s) chosen are highly application-specific and may be readily identified by one of ordinary skill in the art through materials commonly available in the public domain or through routine experimentation (See, e.g., *Buffers. A Guide for the Preparation and Use of Buffers in Biological Systems*, Gueffroy, D., Ed. Calbiochem Corporation (1975); *Scopes, Protein Purification: Principles and Practice* (1982); and Deutscher (1990) "Guide to Protein Purification" in *Methods in Enzymology* vol. 182, and other volumes in this series).

Typically, the sample and the binding moieties are present in a binding buffer. Non-limiting examples of suitable binding buffers include a solution containing 50 mM sodium phosphate and 0.15 M NaCl, pH 7; a solution containing 50 mM sodium phosphate and 0.15 M NaCl, pH 8; and the like. Suitable binding buffers include, e.g., Tris-based buffers, borate-based buffers, phosphate-based buffers, imidazole, HEPES, PIPES, MOPS, MOPSO, MES, TES, acetate, citrate, succinate and the like.

Examples of suitable binding buffers include those that modify surface charge of an analyte and/or binding moieties, such as pH buffer solutions. pH buffer solutions preferably are strong buffers, sufficient to maintain the pH of a solution in the acidic range, i.e., at a pH less than 7, preferably less than 6.8, 6.5, 6.0, 5.5, 5.0, 4.0 or 3.0; or in the basic range at a pH greater than 7, preferably greater than 7.5, 8.0, 8.3, 8.5, 9.0, 9.3, 10.0 or 11.0. The pH conditions suitable for purifying a target protein group from a sample comprising the target protein group and contaminating proteins range from about 3.5 to about 11, from about 4.0 to about 10.0, from about 4.5 to about 9.5, from about 5.0 to about 9.0, from about 5.5 to about 8.5, from about 6.0 to about 8.0, or from about 6.5 to about 7.5. Typically, binding buffers have a pH range of about 6.5 to about 7.5. In an alternative embodiment of the present invention, binding buffers have a pH range of about 6.5 to about 8.5.

Alternatively, binding buffers of various salt concentrations may be used. Exemplary NaCl salt concentrations suitable for purifying a target protein group from a sample comprising the target protein group and contaminating proteins range from about 0.01 M NaCl to about 3 M NaCl, from about 0.05 M NaCl to about 1.5 M NaCl, from about 0.1 M NaCl to about 1.0 M NaCl, or from about 0.2 M NaCl to about 0.5 M NaCl. Preferred binding buffers have a salt concentration in the range of about 0 M to about 0.25 M. Other suitable salts in binding buffers are KCl or NaHOAc.

Other binding buffers suitable for the present invention include combinations of buffer components mentioned above. Binding buffers formulated from two or more of the foregoing binding buffer components are capable of modifying the selectivity of molecular interaction between contaminating proteins and binding moieties.

As will be appreciated by the ordinary skilled in the art, temperature conditions for protein purification may vary depending on the properties of the target protein group of interest to be purified. Typically, temperature conditions suitable for purifying a target protein group from a sample comprising the target protein group and contaminating proteins range from about 4° C. to about 40° C., from about 15° C. to about 40° C., from about 20° C. to about 37° C., or from about 22° C. to about 25° C. Typical temperature conditions are in the range from about 4° C. to about 25° C. One preferred temperature is about 4° C.

Contacting a sample with a library of binding moieties and binding of analytes to the binding moieties is done for a period of time sufficient for binding contaminating proteins and the minority of the target protein to the library of binding moieties. Typically, the library of binding moieties and the sample comprising the target protein group and the contaminating proteins are incubated together for at least about 10 min., usually at least about 20 min., more usually for at least about 30 min., more usually for at least about 60 min. Incubation time may also be for several hours, for example up to 12 hrs, but typically does not exceed about 1 hr. When the methods of the present invention are performed, for example, using a column, the time for contacting a sample with a library of binding moieties is referred to as residence time. A typical residence time range is from about 1 minute to about 20 minutes.

Once analytes have bound to the binding moieties, it may be desirable to elute the analytes for additional analyses. Among efficient elution buffers are those described in Table 1. They can be used singularly or according to a predetermined sequence (e.g., eluents that act on ion exchange effect first, followed by eluents capable to disassemble hydrophobic associations, etc.).

TABLE 1

Scheme of different elution protocols for proteins adsorbed onto solid phase peptide library

| Eluting agent | Composition | Dissociated bonds |
|---|---|---|
| Salt | 1 M Sodium chloride | Ionic interactions |
| Glycols | 50% ethylene glycol in water | Mildly hydrophobic associations |
| Acidic pH | 200 mM Glycine-HCl pH 2.5 | Hydrogen bonding, conformation changes |

TABLE 1-continued

Scheme of different elution protocols for proteins
adsorbed onto solid phase peptide library

| Eluting agent | Composition | Dissociated bonds |
|---|---|---|
| Dissociating-detergent agents | 2 M thiourea-7 M urea-4% CHAPS | Mixed mode, hydrophobic associations, hydrogen bonding |
| Denaturant | 6 M Guanidine-HCl pH 6 | All types of interactions |
| Hydro-organic | Acetonitrile (6.6)-isopropanol (33.3)-trifluoroacetic acid (0.5)-water (49.5) | Strong hydrophobic associations |
| Acidic dissociating agent | 9 M urea, 2% CHAPS, citric acid to pH 3.0-3.5 | Hydrogen bonding, ionic interactions |
| Alkaline dissociating agent | 9 M urea, 2% CHAPS, ammonia to pH 11 | Ionic interactions, hydrogen bonding |

A preferred elution buffer of the present invention includes a matrix material suitable for use in a mass spectrometer. Inclusion of a matrix material in the buffer, some embodiments of the invention may optionally include eluting analyte(s) from binding moieties directly to mass spectrometer probes, such as protein or biochips. In other embodiments of the invention the matrix may be mixed with analyte(s) after elution from binding moieties. Still other embodiments include eluting analytes directly to SEND or SEAC/SEND protein chips that include an energy absorbing matrix predisposed on the protein chip. In these latter embodiments, there is no need for additional matrix material to be present in the elution buffer.

F. Separating and Collecting the Target Protein Group

The present invention provides methods for purifying from a sample a target protein group. These methods comprise the steps of separating an unbound target protein group from the contaminating proteins and target protein group bound to the binding moieties and collecting the unbound target protein group from the sample. The collected target protein group is more pure than the target protein group in the sample.

As described before, a capture agent can be coupled to a solid support either before or after it has contacted a sample. Thus, typically, the methods of the present invention comprise separating an unbound target protein group from the contaminating proteins and target protein group bound to the binding moieties that are coupled to a solid support. This separation may be accomplished in a variety of ways, including, but not limited to, for example, centrifugation, column chromatography, use of linker moieties or use of magnetic beads.

In one embodiment, separation of an unbound target protein group from the contaminating proteins and target protein group bound to the binding moieties that are coupled to a solid support is done by centrifugation. After centrifugation of a sample comprising a target protein group and binding moieties bound to solid supports, proteins bound to the binding moieties will be pelleted. The unbound target protein group will be present in the supernatant from where it can be collected.

In another embodiment, separation of the unbound target protein group from the contaminating proteins and target protein group bound to the binding moieties that is coupled to magnetic beads is by applying a magnetic force. Proteins bound to the binding moieties/magnetic beads will be pulled away from the unbound target protein group. The unbound target protein group will be present in the supernatant from where it can be collected. Magnetic beads, typically, comprise a ferromagnetic oxide particle, such as ferromagnetic iron oxide, maghemite, magnetite, or manganese zinc ferrite (see, e.g., U.S. Pat. No. 6,844,426).

In yet another embodiment, separation of the unbound target protein group from the contaminating proteins and target protein group bound to the binding moieties that are coupled to a solid support is done by column chromatography. After binding the contamination proteins and the minority of the target protein group, the mixture is loaded on a column that retains the solid support and proteins bound thereto. The unbound target protein group will be present in the flowthrough from where it can be collected.

G. Assessing the Purity of the Purified Target Protein Group

Using the methods of the present invention as described herein, a target protein is purified to a desired degree. Applying the methods of the present invention, typically results in a collected target protein group that is more pure than the target protein group in the sample. Thus, the target protein group has been purified further and is at least 96% pure, preferable at least 97%, more preferably at least 98%, and most preferably at least 99% pure.

Assessing the purity of a target protein group purified using the techniques described herein or detecting, quantifying or characterizing it otherwise may be accomplished using any suitable method known to one of ordinary skill in the art (see also Examples). For example, calorimetric assays using dyes are widely available. Alternatively, detection may be accomplished spectroscopically. Spectroscopic detectors rely on a change in refractive index; ultraviolet and/or visible light absorption, or fluorescence after excitation with a suitable wavelength to detect reaction components. Exemplary detection methods include fluorimetry, absorbance, reflectance, and transmittance spectroscopy. Other examples of detection are based on the use of antibodies (e.g., ELISA and Western blotting). Changes in birefringence, refractive index, or diffraction may also be used to monitor complex formation or reaction progression. Particularly useful techniques for detecting molecular interactions include surface plasmon resonance, ellipsometry, resonant mirror techniques, grating-coupled waveguide techniques, and multi-polar resonance spectroscopy. These techniques and others are well known and can readily be applied to the present invention by one skilled in the art, without undue experimentation. Many of these methods and others may be found for example, in "Spectrochemical Analysis" Ingle, J. D. and Crouch, S. R., Prentice Hall Publ. (1988) and "Analytical Chemistry" Vol. 72, No. 17.

Another preferred method for characterizing the purified target protein group is by mass spectroscopy. Mass spectroscopy techniques include, but are not limited to ionization (I) techniques such as matrix assisted laser desorption (MALDI), continuous or pulsed electrospray (ESI) and related methods (e.g., IONSPRAY or THERMOSPRAY), or massive cluster impact (MCI); these ion sources can be matched with detection formats including linear or non-linear reflection time-of-flight (TOF), single or multiple quadropole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of analyte have been detected, for example, using ESI (Valaskovic, G. A. et al., (1996) Science 273:1199-1202) or MALDI (Li, L. et al., (1996) J. Am. Chem. Soc. 118:1662-1663) mass spectrometry. ES mass spectrometry has been introduced by Fenn et al. (J. Phys. Chem. 88, 4451-59 (1984); PCT Application No. WO 90/14148) and current applications are summarized in recent review articles (R. D. Smith et al., Anal. Chem. 62, 882-89 (1990) and B. Ardrey, Electrospray Mass Spectrometry, Spectroscopy Europe, 4, 10-18 (1992)). MALDI-TOF mass spectrometry has been introduced by Hillenkamp et al. ("Matrix Assisted UV-Laser Desorption/Ionization: A New Approach to Mass Spectrometry of Large Biomolecules," *Biological Mass Spectrometry* (Burlingame and McCloskey, editors), Elsevier Science Publishers, Amsterdam, pp. 49-60, 1990). With ESI, the determination of molecular weights in femtomole amounts of sample is very accurate due to the presence of multiple ion peaks that may be used for the mass calculation. A preferred analysis method utilizes Surfaces Enhanced for Laser Desorption/Ionization (SELDI), as discussed for example in U.S. Pat. No. 6,020, 208. Mass spectroscopy is a particularly preferred method of detection in those embodiments of the invention where capturing of analytes directly onto a mass spectrometer probe or biochip occurs, or where a capturing buffer contains a matrix material or is combined with a matrix material after elution of analytes from the binding moieties.

Another method of detection and target protein group characterization widely used is electrophoresis separation based on one or more physical properties of the analyte(s) of interest. A particularly preferred embodiment for analysis of polypeptide and protein analytes is two-dimensional electrophoresis. A preferred application separates the analyte by isoelectric point in the first dimension, and by size in the second dimension. In addition, purified target protein group and the proteins bound to the binding moieties can be analyzed by, for example, SDS-PAGE, followed by staining (see Examples). Methods for electrophoretic analysis of analytes vary widely with the analyte being studied, but techniques for identifying a particular electrophoretic method suitable for a given analyte are well known to those of skill in the art.

A mass spectrometry analysis typically shows protein peaks at particular values of mass-to-charge ratio (m/z). As used herein, a peak is a local maximum in signal intensity, with respect to one or more of m/z, chromatographic retention time, or any other suitable variable. Generally, the intensity value or peak intensity (height, area under the curve, or other suitable intensity measure) are in arbitrary units, with absolute values depending upon a number of factors, such as detector settings. Measuring and comparing the peaks of a sample (i.e., comprising at least 95% of a target protein group and at most 5% of contaminating proteins) to the peaks of a solution comprising a collected target protein purified according to this invention, provides an assessment of purity of the collected target protein group. It is also possible to quantify the collected target protein group by taking, for example, a negative photograph of a gel using Polaroid 665 positive/negative instant film and subjecting the negative photograph to densitometry. Starting with the area under each curve obtained by the densitometric evaluation of each protein band, the purity of the collected target protein group can be calculated.

H. Additional Steps for Purifying the Target Protein Group

Generally, the methods of the present invention can be used in combination with regular separation methods used in downstream processing of a target protein group.

1. Culturing a Host Cell

In a preferred embodiment of the methods of the present invention, the method comprises, before contacting a sample comprising the target protein group with a library of binding moieties, the step of culturing a cell that produces the target protein group. In a preferred embodiment, the cell is a host cell as described above. Preferred culture conditions for a given host cell may be found in the scientific literature and/or from the source of the host cell, such as the American Type Culture Collection.

A host cell for culturing can be a eukaryotic cell or a prokaryotic cell. Methods for culturing host cells are known in the art. Eukaryotic host cells used to produce a target protein group may be cultured in a variety of growth media. Commercially available growth media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the eukaryotic host cells. In addition, any of the media described in Ham et al., Meth. Enz. 58:44 (1979), Barnes et al., Anal. Biochem.102:255 (1980), U.S. Pat. Nos. 4,767,704; 4,657, 866; 4,927,762; 4,560,655; or U.S. Pat. No. 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin®), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Methods for culturing prokaryotic cells, expression of recombinant protein and peptide production are well known in the art (see, e.g., Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology*, Greene Publishing Associates and Wiley Interscience, N.Y. (1994)).

2. Purification of a Prior Sample

In one embodiment of the present invention, the method further comprises, before contacting a sample with a library of binding moieties, the steps of subjecting a prior sample comprising the target protein group and the contaminating proteins to at least one purification step and collecting the sample comprising the target protein group and the contaminating proteins, whereby the target protein group is more pure in the sample than in the prior sample.

A prior sample, comprising less than 95% of a target protein group of interest, may be manipulated in a variety of ways, to enhance its property and to obtain a sample, comprising at least 95% of the target protein group, which can be used in the methods of the present invention. Such manipulations of a prior sample include purification, depletion of certain analytes, concentrating, grinding, extracting, percolating, diluting, filtering, sifting, etc., that improve the purity of the target protein group of interest making it amenable for use in the methods of the present invention. For example, solid samples may be pulverized to a powder, then extracted using an aqueous or organic solvent. The extract from the powder may then be subjected to the methods of the present invention. Gaseous samples may be bubbled or percolated through a solution to dissolve and/or concentrate components of the gas in a liquid prior to subjecting the liquid to methods of the present invention.

Other purification steps include, but are not limited to, filtration, dialysis, precipitation (e.g., ammonium sulphate precipitation, ethanol precipitation); preparative electrokinetic methods (e.g., electrophoresis, isoelectric focusing), liquid chromatography (e.g., anion or cation exchange chromatography, hydroxylapatite chromatography, affinity chromatography using an antibody, hydrophobic interaction chromatography (HIC), reverse phase HPLC, chromatography on silica, chromatofocusing, and gel filtration).

3. Preparing a Pharmaceutical Composition

The target protein group purified according to the methods of the present invention may be used to prepare a pharmaceutical composition that can be used for various therapeutic or other uses known for such target protein group. Thus, in one embodiment of the present invention, the method further comprises the step of preparing a pharmaceutical composition by combining the collected target protein group with a pharmaceutically acceptable carrier.

Such a carrier can be a sterile liquid, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

An oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such pharmaceutical compositions will contain a therapeutically effective amount of a target protein group purified according to the present invention, together with a suitable amount of carrier so as to provide the form for proper administration to a host.

II. Pharmaceutical Compositions

The present invention also provides pharmaceutical compositions. In a preferred embodiment, the pharmaceutical composition comprises a target protein group prepared according to the method of the present invention and a pharmaceutically acceptable carrier.

The target protein group of the pharmaceutical composition can be any protein described herein or known in the prior art. The difference between a target protein prepared according to the methods of the present invention and the target protein group known in the prior art is the degree of purity and the absence of contaminating proteins in a final solution comprising the purified target protein group. As described herein, typically even highly purified protein preparations (see Example 1) comprise contaminating proteins that can not be separated from the target protein group of interest using standard techniques. However, using the methods of this invention to purify a target protein group, the contaminating proteins can be removed almost completely. Thus, a target protein group purified using the methods of the present invention is characterized by a greater degree of purity and thus is more desirable and different from a target protein group purified by other techniques.

A pharmaceutical composition of the present invention, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

III. Kits

The present invention also provides kits for purifying a target protein group. The kits contain components that allow one of ordinary skill in the art to perform the methods described herein. In a preferred embodiment, the kit comprises a library of binding moieties having at least 100 different binding moieties and an instruction to purify a target protein group by contacting a sample comprising at least 95% of the target protein group and at most 5% of contaminating proteins with the library of binding moieties.

The instructions may be present in the subject kits in a variety of forms, one or more of which may be present in the kit. The instruction may be present as printed information on a suitable medium or substrate, e.g., a piece of paper on which the information of how to purify a target protein group by contacting a sample comprising at least 95% of the target protein group and at most 5% of contaminating proteins with the library of binding moieties, is printed. Another form would be a computer readable medium, such as a CD or diskette on which the information of how to purify a target protein group by contacting a sample comprising at least 95% of the target protein group and at most 5% of contaminating proteins with the library of binding moieties, is recorded. Another form may be a website address that may be used by a user of the kit to access via the internet the information of how to purify a target protein group by contacting a sample comprising at least 95% of the target protein group and at most 5% of contaminating proteins with the library of binding moieties.

In another embodiment of the present invention, the kits of the present invention further comprise a plurality of containers retaining incubation buffers for contacting the sample with the library of binding moieties or one or more columns, such as fractionating columns.

In some kit embodiments of the invention, the library of binding moieties is supplied coupled to a solid support, preferably insoluble beads. In other embodiments, the solid support and library of binding moieties are supplied separately. When supplied separately, the library of binding moieties and/or solid support include a linker moiety and/or a complementary linker moiety that allow the operator of the invention to couple the binding moieties to the solid support during the course of practicing the invention described herein. Kits providing separate library of binding moieties and solid supports may optionally comprise additional reagents necessary to perform the coupling of the library of binding moieties to the solid support.

Furthermore, a kit of this invention can include chromatographic media used to purify the target proteins from a prior sample, for subsequent polishing using the library of binding moieties of this invention.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

As can be appreciated from the disclosure above, the present invention has a wide variety of applications. The invention is further illustrated by the following examples, which are only illustrative and are not intended to limit the definition and scope of the invention in any way.

IV. EXAMPLES

Example 1

Separation of Serum Proteins from Purified Myoglobin

Pure muscle myoglobin (Sigma) was first contaminated with human serum proteins and the resulting mixture, comprising 95% of myoglobin (i.e., the target protein group of interest) and at most 5% of contaminating serum proteins, was then polished using a combinatorial peptide library attached to beads. The combinatorial peptide library comprised about 30,000,000 binding moieties.

Myoglobin was dissolved at a concentration of 10 mg/ml in a 25 mM phosphate buffer, pH 7.4. To this solution, 5% albumin-depleted human serum proteins (i.e., the contaminating proteins) were added. This corresponds to at most 5% of the myoglobin present in solution. 400 μL protein solution were then mixed with 80 uL of a combinatorial peptide library attached to a solid phase. The suspension was gently shacked for 60 minutes at room temperature. The supernatant (unbound polished myoglobin) was then separated from the proteins bound to the combinatorial peptide library attached to a solid phase by filtration. The solid phase was washed with the phosphate buffer. Proteins bound to the combinatorial bead library (protein impurities) were then completely desorbed and collected for analysis.

The resulting fractions were analyzed by SDS-PAGE and compared to the initial contaminated myoglobin (FIG. 1). Several protein impurities were clearly visible in the contaminated myoglobin (lane a). They were of different molecular mass and represented about 5% of total proteins; most of them were from added serum and few others were part of the initial pure myoglobin. Lane b, shows the polished myoglobin. Final purity of myoglobin after the polishing using the combinatorial peptide library was higher than before the polishing treatment (compare lanes "a" and "b"). Overall recovery was estimated to be about 95%. Proteins bound to the combinatorial peptide library and then completely desorbed after the polishing are shown in lane c. Many different serum proteins were captured by the combinatorial peptide library including a minority of myoglobin.

This experiment was repeated with similar results using a protein sample of 96.3% myoglobin and 3.7% of contaminating serum proteins.

Example 2

Separation of E. coli Proteins from Purified Myoglobin

Pure muscle myoglobin (Sigma) was first contaminated with soluble E. coli proteins and the resulting mixture, comprising 95% of myoglobin (i.e., the target protein group of interest) and at most 5% of contaminating serum proteins, was then polished using a combinatorial hexapeptide library attached to beads.

100 mg of myoglobin were dissolved in 400 μL of a 25 mM phosphate buffer, pH 7.4. To this solution, 5 mg of soluble E. coli proteins (i.e., the contaminating proteins) were added. The resulting solution was then mixed with 80 μL of a combinatorial hexapeptide library attached to a solid phase. The suspension was gently shacked for 20 minutes at room temperature. The supernatant (unbound polished myoglobin) was then separated from the proteins bound to the combinatorial hexapeptide library attached to a solid phase by centrifugation. The solid phase was washed with the phosphate buffer and collected unbound proteins were then analyzed.

Figure 2:
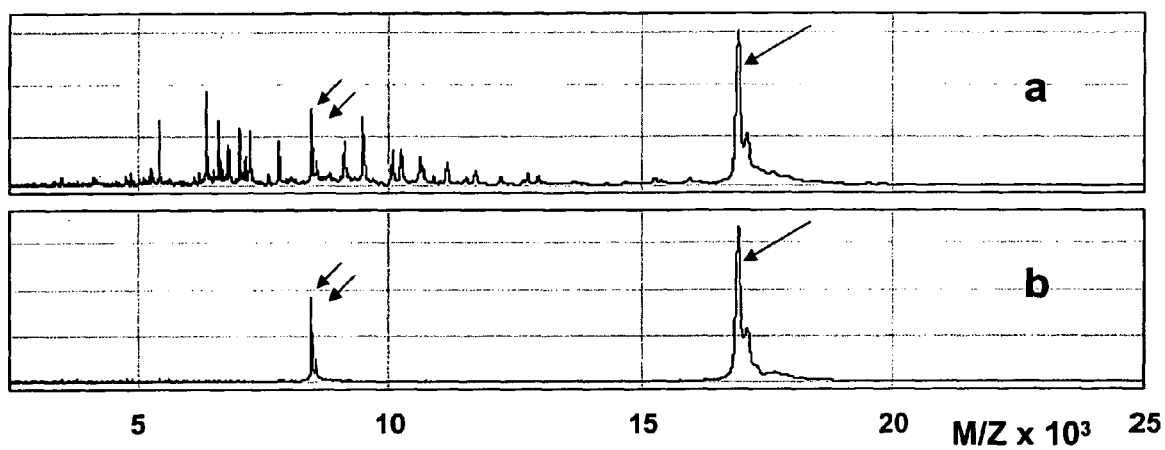
FIG. 2 shows the purification of myoglobin contaminated with 5% of an aqueous extract of *Escherichia coli* using a combinatorial peptide library and the methods of this invention. A. A MALDI mass spectrometry profile is shown. "a": myoglobin contaminated with *E. coli* extract; "b": polished myoglobin collected in the flowthrough. The single arrows in point to myoglobin, the double arrows point to the double size charged myoglobin. B. An SDS-PAGE analysis is shown. The SDS-PAGE shows the following protein fractions: lane "a": myoglobin contaminated with *E. coli* extract; lane "b": polished myoglobin collected in the flowthrough; lane "c": *E. coli* contaminating proteins, including a minority of the myoglobin bound to the combinatorial peptide library; lane "d": standard extract of *E. coli*.
Figure 2:
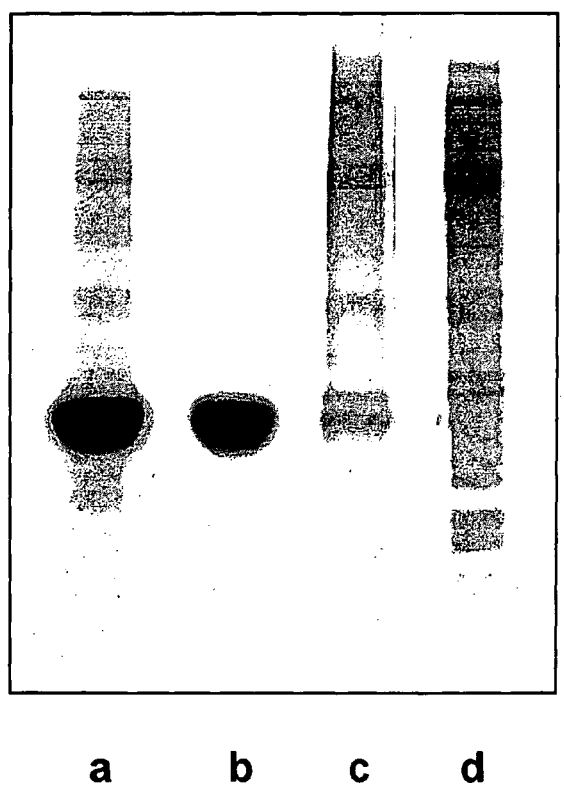

Analysis was accomplished by SELDI MS (FIG. 2A) and SDS-PAGE (FIG. 2B) and compared to the initial contaminated myoglobin (FIG. 2). Several protein impurities were clearly visible in the sample comprising contaminated myoglobin (lane "a"). They were of different molecular mass and represented about 5% of total proteins. Most of these contaminating proteins were from E. coli extract and few others were part of the initial pure myoglobin. Lane "b" of FIGS. 2A and 2B, shows the polished myoglobin. Final purity of myoglobin after the polishing using the combinatorial peptide library was >99% and thus, significantly higher than before the polishing treatment (compare lanes "a" and "b" from both SDS-PAGE and SELDI MS analysis; FIG. 2). Overall recovery was estimated to be about 95%. Proteins bound to the combinatorial peptide library and then completely desorbed after the polishing are shown in FIG. 2B, lane "c" (SDS-PAGE). FIG. 2B, lane "d" shows the initial extract from E. coli for comparison with the desorbed impurities.

Example 3

Separation of P. pastoris Proteins from Purified Recombinant Human Albumin

A solution of purified recombinant human albumin (96%) and P. pastoris proteins (4%) at a concentration of 10 mg/mL was prepared in phosphate buffered saline (PBS). Separately 1 mL column of solid phase combinatorial hexapeptide library was packed, equilibrated with PBS and connected to a chromatographic set up comprising a pumping system and UV/pH detection unit for recording both events at the column outlet.

Figure 3:
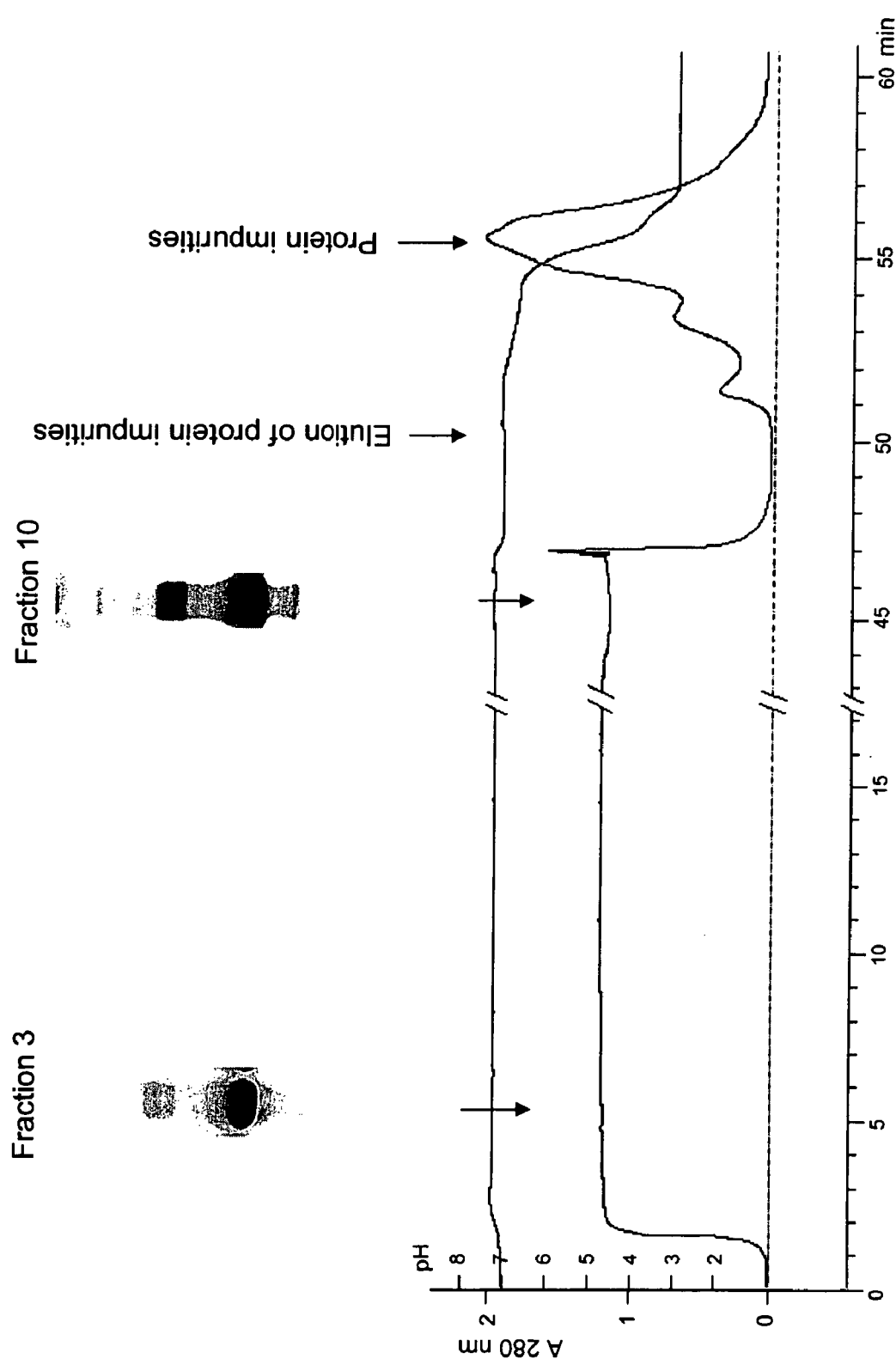
FIG. 3 shows the polishing (removal of contaminants) from recombinant human albumin expressed in *Pichia pastoris*. The separation of impurities was accomplished by frontal analysis of the initial extract (albumin at 96% purity) on a column containing 1 mL of combinatorial peptides. Fractions have been collected and each of them analyzed by SDS-PAGE. The first fractions, including fraction 3 as shown, contained "polished" recombinant albumin while the last fractions contained progressively more and more contaminants as a result of progressive saturation of the combinatorial beads. The begin of elution of protein impurities and the peak fractions including protein impurities are indicated by arrows.

The column was loaded continuously with the recombinant human albumin/P. pastoris protein solution to be polished at a linear flow rate of 50 cm/hour. The flowthrough was collected by fractions of few mL each to analyze the capability of the solid phase to remove protein impurities likewise a frontal analysis. Once the load was terminated, a PBS solution was introduced for washing out excess of proteins. Collected fractions were then analyzed by SDS-PAGE and mass spectrometry. Results indicated that the first three fractions contained pure albumin while the remaining fractions progressively contained more and more contaminating proteins as a result of the saturation of the combinatorial beads column. FIG. 3 shows the entire chromatogram along with electrophoresis analysis of certain fractions.

Example 4

Purification of a Target Protein Group

The methods of the present invention are suitable to purify a target protein group from, for example, a 25 liter sample comprising at least 95% of the target protein group and at most 5% of contaminating proteins wherein the contaminating proteins are present at a concentration of between $10^{-6}$ M to about $10^{-12}$ M and comprise about 40 detectable but undefined individual contaminating proteins in the solution. To this sample 0.5 liter beads comprising a combinatorial peptide library of about 30,000,000 peptide binding moieties is added at a concentration of 50 μMol analyte per ml beads.

INCORPORATION BY REFERENCE

All publications, patents and patent applications cited in this specification are herein incorporated in their entirety by reference as if each individual publication, patent or patent application were specifically and individually indicated to be incorporated by reference.

What is claimed is:

1. A method for purifying a target protein group comprising the steps of:
    (a) contacting a sample comprising at least 95% of the target protein group and at most 5% of contaminating proteins with a library comprising at least 100 different binding moieties in an amount sufficient to bind a majority of the contaminating proteins and a minority of the target protein group, but not a majority of the target protein group;
    (b) binding the majority of the contaminating proteins and the minority of the target protein group, but not the majority of the target protein group, to the library of binding moieties;
    (c) separating the unbound majority of the target protein group from the majority of the contaminating proteins and the minority of the target protein group bound to the library of binding moieties; and
    (d) collecting the unbound majority of the target protein group which is more pure than the target protein group in the sample.

2. The method according to claim 1, wherein the sample comprises at least 98% of the target protein group and at most 2% of contaminating proteins.

3. The method according to claim 1, wherein the sample comprises a fermentation broth.

4. The method according to claim 1, wherein the target protein group consists of a single protein species.

5. The method according to claim 1, wherein the target protein group comprises a recombinant protein.

6. The method according to claim 5, wherein the recombinant protein is selected from the group consisting of an enzyme, a hormone, a growth factor, a receptor, a vaccine, an immunoglobulin and fragments of any of the foregoing.

7. The method according to claim 5, wherein the recombinant protein is selected from the group consisting of vascular endothelial growth factor (VEGF), platelet-derived growth factor (PDGF), fibroblast growth factor (FGF), epidermal growth factor (EGF), transforming growth factor (TGF), insulin-like growth factor (IGF), erythropoietin (EPO), bone morphogenetic protein (BMP), bone-derived neurotrophic factor (BDNF), colony stimulating factor (CSF), nerve growth factor (NGF), human growth hormone (hGH), tumor necrosis factor (TNF), insulin, tissue-type plasminogen activator (t-PA), interferon, interleukin (IL) and herceptin.

8. The method according to claim 1, wherein the target protein group comprises a naturally occurring protein.

9. The method according to claim 1, wherein the library comprises at least 1,000, at least 10,000, at least 100,000, at least 1,000,000, at least 10,000,000 or at least 100,000,000 different binding moieties.

10. The method according to claim 1, wherein the library is a non-selective library selected from the group consisting of a germ line antibody library, a phage display library of recombinant polypeptides, a dye library, a non-combinatorial library, a combinatorial library and portions of any of the foregoing.

11. The method according to claim 10, wherein the library comprises at least a portion of a combinatorial library.

12. The method according to claim 11, wherein the combinatorial library comprises binding moieties selected from polypeptides, peptides, hexapeptides, polynucleotides, lipids, oligosaccharides and small organic molecules.

13. The method according to claim 11, wherein the combinatorial library is a combinatorial library of hexapeptides.

14. The method according to claim 1, wherein the binding moieties comprise bio-organic polymers.

15. The method according to claim 1, wherein the binding moieties are selected from the group consisting of dyes, polypeptides, peptides, hexapeptides, antibodies, nucleic acids, aptamers and small organic molecules.

16. The method according to claim 1, wherein the binding moieties are bound to a solid support or supports.

17. The method according to claim 16, wherein the solid support or supports is a collection of beads or particles.

18. The method according to claim 16, wherein the solid support or supports are selected from the group consisting of beads, fibers, filters, membranes and monoliths.

19. The method according to claim 16, wherein each binding moiety is attached to a different solid support.

20. The method according to claim 16, wherein a plurality of different binding moieties are attached to a single solid support.

21. The method according to claim 1, further comprising, before step (a), the step of culturing a cell that produces the target protein group.

22. The method according to claim 21, wherein the cell is a eukaryotic cell.

23. The method according to claim 21, wherein the cell is a prokaryotic cell.

24. The method according to claim 21, wherein the sample is a cell supernatant.

25. The method according to claim 21, wherein the sample is a cell extract.

26. The method according to claim 1, further comprising, before step (a), the steps of:
    (i) subjecting a prior sample comprising less than 95% of the target protein group and more than 5% of the contaminating proteins to at least one purification step; and
    (ii) collecting the sample comprising at least 95% of the target protein group and at most 5% of the contaminating proteins.

27. The method according to claim 1, further comprising the step of:
    (e) preparing a pharmaceutical composition by combining the collected target protein group with a pharmaceutically acceptable carrier.

28. The method according to claim 1, wherein step (a) is done in a suspension batch process.

29. The method according to claim 1, wherein step (a) is done by passing the sample over a column packed with the library of binding moieties attached to a solid support.

30. The method according to claim 1, wherein step (a) comprises a fluidized bed process.

* * * * *